(12) United States Patent
Jonsson

(10) Patent No.: US 12,275,363 B2
(45) Date of Patent: Apr. 15, 2025

(54) METHOD FOR OPEN AIRWAY POSITION AFTER A VEHICLE CRASH

(71) Applicants: Ningbo Geely Automobile Research & Development Co., Ltd., Ningbo (CN); Zhejiang Geely Holding Group Co., Ltd., Zhejiang (CN)

(72) Inventor: Björn Jonsson, Gothenburg (SE)

(73) Assignees: Ningbo Geely Automobile Research & Dev. Co., Ltd., Ningbo (CN); ZHEJIANG GEELY HOLDING GROUP CO., LTD., Zhejiang (CN)

( * ) Notice: Subject to any disclaimer, the term of this patent is extended or adjusted under 35 U.S.C. 154(b) by 193 days.

(21) Appl. No.: 18/138,088

(22) Filed: Apr. 23, 2023

(65) Prior Publication Data

US 2023/0264642 A1    Aug. 24, 2023

Related U.S. Application Data

(63) Continuation of application No. PCT/CN2021/127389, filed on Oct. 29, 2021.

(30) Foreign Application Priority Data

Nov. 11, 2020 (EP) .................................. 20206963

(51) Int. Cl.
*B60R 21/0134* (2006.01)
*A61B 5/00* (2006.01)
(Continued)

(52) U.S. Cl.
CPC ........ *B60R 21/0136* (2013.01); *A61B 5/6893* (2013.01); *B60N 2/0276* (2013.01);
(Continued)

(58) Field of Classification Search
CPC ........................ B60R 21/0134; B60R 21/0136
See application file for complete search history.

(56) References Cited

U.S. PATENT DOCUMENTS 5,810,417 A *  9/1998  Jesadanont  ............. B60R 22/26
                                                     296/68.1
6,076,887 A    6/2000  Andersson
(Continued)

FOREIGN PATENT DOCUMENTS

CN    105584444 A    5/2016
CN    107933495 A    4/2018
(Continued)

OTHER PUBLICATIONS

International Search Report from corresponding International Application No. PCT/CN2021/127389, mailed on Jan. 27, 2022, 2 pages.

*Primary Examiner* — Long T Tran
(74) *Attorney, Agent, or Firm* — Tucker Ellis LLP

(57) ABSTRACT

A computer-implemented method for moving an occupant of a vehicle seat to open airway position after a vehicle crash event. The vehicle seat having a seat cushion, a backrest and a headrest. The method includes detecting occurrence of a vehicle crash event, and moving at least a portion of the backrest and/or headrest backwards and pulling an occupant of the vehicle seat backwards towards the backrest by powered retraction of a seat belt of the occupant by means of a seat belt retractor.

16 Claims, 9 Drawing Sheets

(51) Int. Cl.
*B60N 2/02* (2006.01)
*B60N 2/888* (2018.01)
*B60R 21/0136* (2006.01)
*B60R 21/015* (2006.01)
*B60R 22/195* (2006.01)
*B60N 2/22* (2006.01)
*B60R 21/00* (2006.01)
*B60R 21/01* (2006.01)
*B60R 21/013* (2006.01)
*B60R 22/22* (2006.01)
*B60R 22/24* (2006.01)

(52) U.S. Cl.
CPC ........ *B60N 2/888* (2018.02); *B60R 21/01552* (2014.10); *B60R 22/195* (2013.01); *B60N 2/2222* (2013.01); *B60R 2021/0027* (2013.01); *B60R 2021/01272* (2013.01); *B60R 2021/01315* (2013.01); *B60R 2022/1957* (2013.01); *B60R 22/22* (2013.01); *B60R 22/24* (2013.01)

(56) References Cited

U.S. PATENT DOCUMENTS

| | | | |
|---|---|---|---|
| 6,530,622 | B1 | 3/2003 | Ekern |
| 11,059,450 | B2 * | 7/2021 | Ohno ................ B60R 22/26 |
| 2010/0187881 | A1 | 7/2010 | Fujita |
| 2011/0221247 | A1 | 9/2011 | Hashimoto |
| 2014/0188347 | A1 * | 7/2014 | Tabe ............... B60R 21/01516 701/45 |
| 2014/0217788 | A1 * | 8/2014 | Norwood ............ B60N 2/888 297/216.12 |
| 2017/0267136 | A1 | 9/2017 | Dimovski |
| 2018/0105136 | A1 * | 4/2018 | Goto .................. B60R 21/013 |
| 2020/0114867 | A1 * | 4/2020 | Ryl ..................... B60R 22/48 |
| 2020/0247355 | A1 * | 8/2020 | Kuzumaki ........... B60R 21/013 |
| 2021/0076971 | A1 * | 3/2021 | Oloumi ............... A61B 5/0205 |
| 2021/0153754 | A1 * | 5/2021 | Ozawa ................ A61B 5/0261 |
| 2021/0309124 | A1 * | 10/2021 | Fields ................. B60N 2/0276 |

FOREIGN PATENT DOCUMENTS

| | | |
|---|---|---|
| CN | 110276932 A | 9/2019 |
| CN | 111516636 A | 8/2020 |
| DE | 102011122203 A1 | 6/2013 |
| DE | 102013014478 A1 | 3/2015 |
| EP | 3309018 A1 | 4/2018 |
| EP | 3428005 A1 | 1/2019 |
| JP | 2008238910 A | 10/2008 |
| WO | 2008037313 A1 | 4/2008 |

* cited by examiner

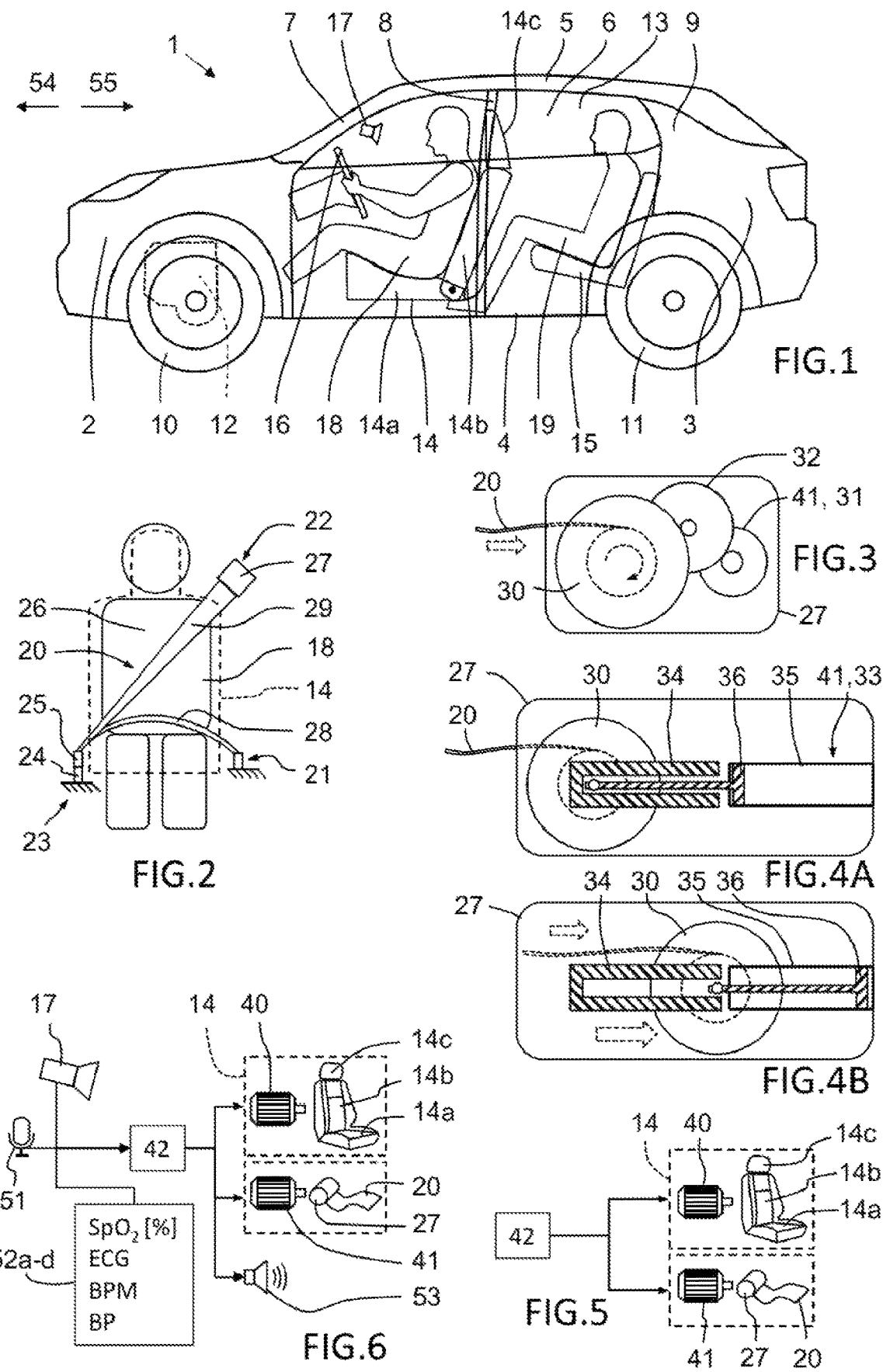

METHOD FOR OPEN AIRWAY POSITION AFTER A VEHICLE CRASH

RELATED APPLICATION DATA

This application is a continuation of International Patent Application No. PCT/CN2021/127389, filed Oct. 29, 2021, which claims the benefit of European Patent Application No. 20206963.9, filed Nov. 11, 2020, the disclosures of which are incorporated herein by reference in their entireties.

TECHNICAL FIELD

The present disclosure relates to computer-implemented method for moving an occupant of a vehicle seat to open airway position after a vehicle crash event. The disclosure further relates to a corresponding vehicle seat system. The method and system according to the disclosure can for example be installed or implemented in a car, a truck, a bus, a rail vehicle, a flying vehicle, a working vehicle or the like.

BACKGROUND

In the field of vehicles there is a continuous demand for further improved safety of the vehicle occupants. For example, safety systems and methods for avoiding vehicle crashes or collisions are developed, as well as safety systems and methods for protecting the vehicle occupants in case of an unavoidable vehicle crash or collision.

For example, document US 2011/221247 A1 appears to describe a vehicle seat system that, upon detection of an imminent collision, first quickly automatically adjusts the backrest forwards, and after the collision has occurred, slowly automatically adjusts the backrest rearwards for minimizing any annoyance caused by the seat belt.

However, despite the activities in the field, there is still a demand for further improved seat systems and associated method in terms of driver and passenger safety in vehicles.

SUMMARY

In the event of a severe vehicle crash event, a strong vehicle structure, seat belt system and air bags may prevent the vehicle occupant, such as for example the driver, from serious injuries. However, there is a risk that the occupant may become unconscious in a body posture that results in hindered airway, i.e. hindered air passage between the occupant's lungs and mouth and/or nose. For example, the head of the occupant may be strongly forward leaning while the torso in still relatively upright sitting, or the head of the occupant may be strongly forward leaning in combination with a forward leaning torso. In such scenarios, the airway passage in the throat region may be restricted or even blocked.

An object of the present disclosure is thus to provide a method and system where the problem of hindered airway of an occupant after a vehicle collision is avoided. This object is at least partly achieved by the features of the independent claims.

According to a first aspect of the present disclosure, there is provided a computer-implemented method for moving an occupant of a vehicle seat to open airway position after a vehicle crash event, the vehicle seat having a seat cushion, a backrest and a headrest, the method comprising: detecting occurrence of a vehicle crash event; and moving at least a portion of the backrest and/or headrest backwards and pulling an occupant of the vehicle seat backwards towards the backrest by powered retraction of a seat belt of the occupant by means of a seat belt retractor (27).

According to a second aspect of the present disclosure, there is provided a vehicle seat system for moving an occupant of a vehicle seat to open airway position after a vehicle crash event. The vehicle seat system comprises a seat having a seat cushion, a backrest and a headrest, wherein the seat further has one or more power actuators configured for adjusting a moving position of the backrest and/or headrest. In addition, the vehicle seat system further comprises a seat belt arrangement having a seat belt and a seat belt retractor, wherein the seat belt arrangement further has power source drivingly connected to the seat belt retractor for enabling powered retraction. Moreover, the vehicle seat system further comprises an electronic control system operatively connected to the one or more power actuators of the seat and power source of the seat belt arrangement. The control system is configured for: determining occurrence of a vehicle crash event; and controlling operation of the one or more power actuators of the seat for moving at least a portion of the backrest and/or headrest backwards and controlling operation of the power source of the seat belt retractor for pulling the occupant of the vehicle seat backwards towards the backrest.

In other words, it may in certain situations be desirable to change the body posture of the occupant after a vehicle collision to a more rearwards and reclined sitting position, because this sitting position generally results in more open airway due to more rearwards inclined head position relative to the torso.

One approach for moving for example an unconscious occupant of a vehicle seat to a more open airway position, i.e. from a position with forwards leaning head to a position with upright or even rearwards leaning head, is to recline the seat, i.e. moving the backrest rearwards. Moreover, for avoiding that the torso and head of the occupant nevertheless remains in a forward leaning body posture, the seat belt may be used for pulling the occupant rearwards, such that the occupant after completed reclining and pulling in the seat belt sits in a relaxed and reclined seating position with the head resting against the headrest, thereby reducing the risk for respiration problems caused by hindered or even blocked airway.

Further advantages are achieved by implementing one or several of the features of the dependent claims.

In some example embodiments, the step of detecting occurrence of a vehicle crash event is performed by: monitoring vehicle acceleration level and detecting occurrence of a vehicle crash event when monitored vehicle acceleration level exceeds a threshold value, or monitoring, or receiving information about, deployment of an airbag within the vehicle. Thereby, two alternative solutions for reliably detecting a crash event are provided, that even may be combined to provide further certainty.

In some example embodiments, the method comprises an intermediate step of waiting a certain time period after the step of detecting occurrence of a vehicle crash event and before initiating the step of moving at least a portion of the backrest and/or headrest backwards and pulling an occupant of the vehicle seat backwards towards the backrest. Thereby, the seat belt arrangement and seat may by controlled, adjusted and set for best protecting the occupant during the crash event, without potential interference by the open airway method.

In some example embodiments, the time period is at least 3 seconds, specifically at least 5 seconds, or within a range of 3-30 seconds, specifically within a range of 5-15 seconds.

These time period and ranges are deemed corresponding to a sufficient long time for the having arrived at the end of the crash event, while also not waiting too long in case of hindered or blocked airway of the occupant.

In some example embodiments, the method comprises an intermediate step of obtaining information about airway status of the occupant, and wherein the method progresses to said step of moving at least a portion of the backrest and/or headrest backwards and pulling an occupant of the vehicle seat backwards towards the backrest when the detected airway status indicates blocked or hindered airway. Thereby, backwards motion of the backrest and pulling of the seat belt may be avoided in case the there is no need for rearrangement of the occupant, or if the harm caused by rearrangement of the occupant is deemed greater than the benefit in terms of improved respiration.

Alternatively, or in combination with above, the method may in some example embodiments comprise an intermediate step of obtaining information about level of consciousness of the occupant, wherein the method progresses to said step of moving at least a portion of the backrest and/or headrest backwards and pulling an occupant of the vehicle seat backwards towards the backrest when the detected level of consciousness of the occupant is low or non-existing, i.e. unconscious. Respiration problems are generally connected with an unconsciousness situation of the occupant. Hence, the consciousness level may be used for evaluating the need or benefit of the rearrangement to a more reclined seat position of the occupant.

Alternatively, or in combination with above, the method may in some example embodiments comprise an intermediate step of obtaining information about values of one or more health parameters associated with the respiratory and/or cardiovascular systems of the occupant, and wherein the method progresses to said step of moving at least a portion of the backrest and/or headrest backwards and pulling an occupant of the vehicle seat backwards towards the backrest when the detected values of the one or more health parameters is outside of a predetermined range. Health parameters associated with the respiratory and/or cardiovascular systems of the occupant are generally relevant parameters for evaluating and determining respiration problems of the occupant, and detection and evaluation of said health parameters may thus be a reliable indication about the need for rearrangement of the occupant.

Alternatively, or in combination with above, the method may in some example embodiments comprise an intermediate step of obtaining information about body posture of the occupant, and wherein the method progresses to said step of moving at least a portion of the backrest and/or headrest backwards and pulling an occupant of the vehicle seat backwards towards the backrest when the detected body posture indicates blocked airway. For example, a stationary, non-moving, forward leaning body posture of head posture may be used as an indicator for both unconsciousness and hindered airway.

In some example embodiments, the motion of at least a portion of the backrest and/or headrest backwards is continued until arriving at a predetermined reclined seat position. Thereby, sufficient rearrangement of the occupant to a more laid back and open airway body posture may be ensured.

Alternatively, in some example embodiments the method comprises monitoring body posture of the occupant during motion of at least a portion of the backrest and/or headrest backwards and pulling the occupant of the vehicle seat backwards towards the backrest, and stopping the motion and pulling when the monitored body posture corresponds to an acceptable body posture in view of open airway of the occupant. Thereby, sufficient rearrangement of the occupant to obtain a desired more laid back and open airway body posture is accomplished without unnecessary movement of the body of the occupant in view of other injuries that may harmed by occupant body rearrangement.

In some example embodiments, the method comprises detecting an occupancy status of a vehicle seat located behind the seat of the occupant, and determining the reclined seat position taking into account the detected occupancy status of the vehicle seat located behind the seat of the occupant. Hence, the occupant is rearranged backwards to a more rearwards inclined seating position as much as possible without causing injuries or harmful interference with a further vehicle occupant that is seated behind the occupant.

In some example embodiments, the step of moving at least a portion of the backrest and/or headrest backwards involves performing one, two, three, or all of the following activities: folding the backrest backwards around a first pivot shaft located in an intersection region of the seat cushion and backrest; moving the headrest backwards; tilting the seat cushion backwards; or adjusting a lumbar support arrangement or multi-contour arrangement of the vehicle seat for protruding more towards a lumbar region and/or back region of the occupant of the vehicle seat. All these measures, separately and jointly, generally results in rearranged seating position of the occupant to a more rearwards inclines body posture that is beneficial in view of improved open airway.

In some example embodiments, the backrest includes a second pivot shaft arranged in a region between the first pivot shaft and the headrest, and wherein the step of moving at least a portion of the backrest and/or headrest backwards additionally involves folding the backrest backwards around the second pivot shaft. Thereby, an even more rearwards curved body posture of the occupant may be accomplished, thereby further enhancing the open airway position while also avoiding too much space or intrusion on the rear side of the seat.

In some example embodiments, the vehicle seat includes one or more power actuators configured for adjusting the position of the backrest and/or headrest, and wherein the step of moving at least a portion of the backrest and/or headrest backwards involves controlling operation of said one or more power actuators for moving at least a portion of the backrest and/or headrest backwards.

In some example embodiments, a seat belt associated with the vehicle seat has a first attachment point for fastening a waist portion of the seat belt to the seat or vehicle chassis, and a second attachment point for fastening a chest portion of the seat belt to the seat or vehicle chassis, wherein the seat belt retractor is located at the second attachment point and configured for powered retraction or tensioning of the chest portion of the seat belt, and wherein the second attachment point is arranged: at the B-pillar of the vehicle chassis, or at the floor of the vehicle chassis, or at an interior side of the roof of the vehicle chassis, or integrated in the vehicle seat, in particular in the backrest or headrest of the vehicle seat.

In some example embodiments, the backrest or headrest comprises a seat belt guide configured for guiding or deflecting the chest portion of the seat belt along its path towards the seat belt retractor. Thereby, an appropriate and effective pulling process may be provided by the seat belt arrangement, that is also largely independent on backrest inclination status and positioning of the seat belt retractor.

In some example embodiments, motion of at least a portion of the backrest and/or headrest backwards and pulling an occupant of the vehicle seat backwards towards the backrest by powered retraction of the seat belt are performed simultaneously and/or consecutively. This specific control strategy for rearranging the occupant to have a more backwards inclined body posture may be selected according to the specific circumstances.

In some example embodiments, the step of moving at least a portion of the backrest and/or headrest backwards and pulling an occupant of the vehicle seat backwards towards the backrest by powered retraction of the seat belt is performed by, during a first half of the motion sequence, primarily pulling the occupant of the vehicle seat backwards towards the backrest by powered retraction of the seat belt while keeping the backrest and/or headrest relatively stationary, and subsequently during a second half of the motion sequence, primarily moving at least a portion of the backrest and/or headrest backwards while ensuring that the occupant remains in close contact with, or adjacent to, the backrest and/or headrest. In general, it may be beneficial to avoid uncontrolled rearwards falling of the occupant body into an already completely rearwards folded backrest. Hence, by keeping the body of the occupant relatively close the backrest during the rearwards folding sequence of the backrest, a more controlled rearrangement of the occupant may be accomplished.

In some example embodiments, the vehicle seat has a first pivot shaft located in an intersection region of the seat cushion and backrest and configured for enabling folding of the backrest backwards, and a second pivot shaft arranged in a region of the backrest located between the first pivot shaft and the headrest and configured for enabling folding of an upper portion of the backrest located between the second pivot shaft and headrest backwards.

In some example embodiments, the seat belt has a first attachment point for fastening a waist portion of the seat belt to the seat or vehicle chassis, and a second attachment point for fastening a chest portion of the seat belt to the seat or vehicle chassis, wherein the seat belt retractor is located at the second attachment point and configured for powered winding or tensioning of the chest portion of the seat belt, and wherein the second attachment point is arranged: at the B-pillar of the vehicle chassis, or at the floor of the vehicle chassis, or at an interior side of the roof of the vehicle chassis, or integrated in the vehicle seat, in particular in the backrest or headrest of the vehicle seat.

In some example embodiments, the seat includes a three-point seat belt arrangement, or the vehicle includes a three-point seat belt arrangement associated with the vehicle seat, wherein the seat belt, when correctly used by an occupant, is configured for extending from a first attachment point, across a waist of the occupant to a connector tongue, and further across the chest of the occupant to a seat belt retractor.

In some example embodiments, the vehicle seat system further comprises a vehicle acceleration sensor, wherein the control system is configured for detecting occurrence of a vehicle crash event by monitoring vehicle acceleration level by means of the vehicle acceleration sensor and detecting occurrence of a vehicle crash event when monitored vehicle acceleration level exceeds a threshold value.

In some example embodiments, the control system is configured for obtaining information about airway status of the occupant, and for moving at least a portion of the backrest and/or headrest backwards and pulling an occupant of the vehicle seat backwards towards the backrest when the detected airway status indicates blocked or hindered airway.

In some example embodiments, the control system is configured for obtaining information about level of consciousness of the occupant, and moving at least a portion of the backrest and/or headrest backwards and pulling an occupant of the vehicle seat backwards towards the backrest when the detected level of consciousness of the occupant is low or non-existing.

In some example embodiments, the control system is configured for obtaining information about values of one or more health parameters associated with the respiratory and/or cardiovascular systems of the occupant, and moving at least a portion of the backrest and/or headrest backwards and pulling an occupant of the vehicle seat backwards towards the backrest when the detected values of the one or more health parameters is outside of a predetermined range.

In some example embodiments, the control system is configured for obtaining information about body posture of the occupant, and moving at least a portion of the backrest and/or headrest backwards and pulling an occupant of the vehicle seat backwards towards the backrest when the detected body posture indicates blocked airway.

In some example embodiments, the control system is configured for moving of at least a portion of the backrest and/or headrest backwards until arriving at a predetermined reclined seat position, or wherein the control system is configured for monitoring body posture of the occupant during motion of at least a portion of the backrest and/or headrest backwards and pulling the occupant of the vehicle seat backwards towards the backrest, and stopping the motion and pulling when the monitored body posture corresponds to an acceptable body posture in view of open airway of the occupant.

In some example embodiments, the control system is configured for detecting an occupancy status of a vehicle seat located behind the seat of the occupant, and determining the reclined seat position taking into account the detected occupancy status of the vehicle seat located behind the seat of the occupant.

In some example embodiments, the backrest or headrest comprises a seat belt guide configured for guiding or deflecting the chest portion of the seat belt along its path towards the seat belt retractor.

In some example embodiments, the control system is configured for, simultaneously and/or consecutively, moving at least a portion of the backrest and/or headrest backwards and pulling an occupant of the vehicle seat backwards towards the backrest by powered retraction of the seat belt.

In some example embodiments, the control system is configured for moving at least a portion of the backrest and/or headrest backwards and pulling an occupant of the vehicle seat backwards towards the backrest by powered retraction of the seat belt, wherein the control system is configured for, during a first half of the motion sequence, primarily pulling the occupant of the vehicle seat backwards towards the backrest by powered retraction of the seat belt while keeping the backrest and/or headrest relatively stationary, and subsequently during a second half of the motion sequence, primarily moving at least a portion of the backrest and/or headrest backwards while ensuring that the occupant remains in close contact with, or adjacent to, the backrest and/or headrest.

The disclosure further relates to a vehicle seat system for moving an occupant of a vehicle seat to an open airway position after a vehicle crash event. The vehicle seat system comprising: a seat having a seat cushion, a backrest and a headrest, wherein the seat further has one or more power actuators configured for adjusting a motion position of the backrest and/or headrest; a seat belt arrangement having a seat belt and a seat belt retractor, wherein the seat belt arrangement further has power source drivingly connected to the seat belt retractor for enabling powered retraction; and an electronic control system operatively connected to the one or more power actuators of the seat and power source of the seat belt arrangement; wherein the control system is configured for performing the method steps described above.

The disclosure further relates to a vehicle comprising the vehicle seat system as described above.

The disclosure further relates to a data processing control system comprising a processor configured to perform the various alternative embodiments of the method described above.

The disclosure further relates to a computer program comprising instructions, which, when the program is executed by a computer, cause the computer to carry out the method as described above.

Further features and advantages of the invention will become apparent when studying the appended claims and the following description. The skilled person in the art realizes that different features of the present disclosure may be combined to create embodiments other than those explicitly described hereinabove and below, without departing from the scope of the present disclosure.

BRIEF DESCRIPTION OF THE DRAWINGS

The disclosure will be described in detail in the following, with reference to the attached drawings, in which FIG. 1 shows schematically a side view of the vehicle having a seat system according to the disclosure, FIG. 2 shows schematically a typical arrangement of a three-point seat belt, FIG. 3 shows schematically a first example embodiment of a powered retractor for the seat belt arrangement, FIGS. 4A-4B show schematically two operating positions of a second example embodiment of a powered retractor for the seat belt arrangement, FIG. 5 shows schematically a first example embodiment of the seat system according to the disclosure, FIG. 6 shows schematically a second example embodiment of the seat system according to the disclosure.

DETAILED DESCRIPTION

Figure 7A:
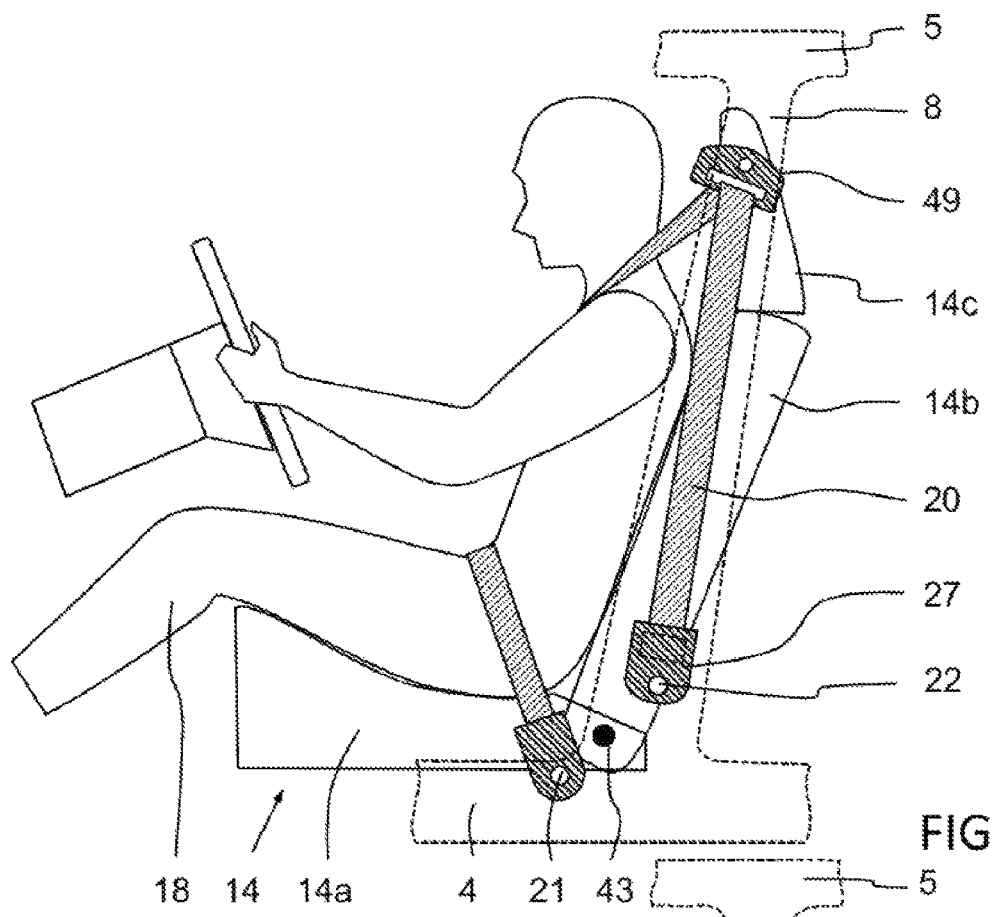
FIGS. 7A-7D show schematically different body postures and corresponding seat positions of a rearrangement sequence of the occupant to more rearwards inclined body posture, according to the disclosure.

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure.

Those skilled in the art will appreciate that the steps, services and functions explained herein may be implemented using individual hardware circuitry, using software functioning in conjunction with a programmed microprocessor or general purpose computer, using one or more Application Specific Integrated Circuits (ASICs) and/or using one or more Digital Signal Processors (DSPs). It will also be appreciated that when the present disclosure is described in terms of a method, it may also be embodied in one or more processors and one or more memories coupled to the one or more processors, wherein the one or more memories store one or more programs that perform the steps, services and functions disclosed herein when executed by the one or more processors.

For setting the method and vehicle seat system of the disclosure in a proper context, FIG. 1 shows an example of a vehicle that may be equipped with the method and seat system according to the disclosure.

Specifically, FIG. 1 schematically shows a vehicle 1 defining a forwards direction 54, a rearwards direction 55 and having a rigid vehicle chassis made of for example steel, aluminium or carbon fibres, or mixtures thereof. The vehicle chassis, also known as Body In White, may for example have a front structure 2, a rear structure 3, a floor structure 4, a roof structure 5, windows 6, A-pillars 7, B-pillars 8 and C-pillars 9. Furthermore, the vehicle 1 may have front wheels 10, rear wheels 11, a propulsion source 12 and a passenger compartment 13 with front seats 14, rear seats 15 and a steering wheel 16. The vehicle according to the example embodiment of FIG. 1 further has at least one image detector 17 within the passenger compartment and configured for detecting occupants, or for identifying seats with an occupant, or for detecting occupant body posture after a crash event, etc.

In FIG. 1, an occupant 18, i.e. a person, is sitting in the front seat 14, and a further occupant 19 is sitting in a rear seat 15. Each seat may be provided with a seat cushion 14a, a backrest 14b and a headrest 14c.

Each vehicle seat 14, 15 may be provided with a seat belt arrangement, such as a three-point belt arrangement, or four or five point belt arrangements.

FIG. 2 schematically illustrates a seat 14 with a seated occupant 18 being belted by a three-point seat belt arrangement. The seat belt arrangement comprises a seat belt 20 extending between a first attachment point 21 and a second attachment point 22 and a connector tongue 25 secured to the seat belt 20 and configured for being disconnectably coupled to a connector 24 located a third attachment point 23.

The seat belt arrangement may be partly or completely part of the seat 14, i.e. all or some of the first to third attachment points 21-23 may be arranged on the seat 14. Alternatively, some or all of the first to third attachment points 21-23 may be arranged on the vehicle chassis, such that the vehicle 1 includes a three-point seat belt arrangement associated with the vehicle seat 14.

As illustrated in FIG. 2, the seat belt arrangement, when correctly used by an occupant 18, is configured for extending from the first attachment point 21, across a waist of the occupant 18 to a connector tongue 25 coupled to a connector 24 located at the third position 23, and further across the chest 26 of the occupant 18, and subsequently to a seat belt retractor 27 located at the second position 22.

As a result, waist portion 28 of the seat belt 20 extends between the first attachment point 21, across a waist of the occupant 18, and the connector 24 located at the third position 23, and a chest portion 29 of the seat belt 20 extends between the connector 24 located at the third position 23 and the seat belt retractor 27 located at the second position 22.

The seat belt retractor 27 may include a spring loaded reel having a portion of the seat belt 20 wound, and enabling manual pulling out seat belt from the retractor 27 during use, and automatic retraction, i.e. winding up of any slack in the seat belt 20 upon removal of the seat belt 20.

In contrast to conventional retractors, the seat belt retractor 27 according to the present disclosure includes powered retraction of a seat belt. In other words, the seat belt retractor 27, or the seat belt arrangement, has power source 41 drivingly connected to the seat belt retractor 27 for enabling powered retraction of the seat belt 20.

Powered retraction of the seat belt may be implemented in various ways. For example, a first example embodiment of the power seat belt retractor is schematically illustrated in FIG. 3. This retractor has a reel 30 for winding and holding seat belt 20 thereon and a power source 41 in form of an electrical motor 31 driving connected to the reel 30 for enabling powered rotation of the reel 30. A transmission 32 may be drivingly arranged between electric motor 31 and reel 30 if necessary. Upon operation of the electric motor 31 in proper direction the reel 30 will start to rotate and winding up the seat belt, thereby accomplishing powered retraction.

A second example embodiment of the power seat belt retractor is schematically illustrated in FIGS. 4A and 4B. FIG. 4A shows the retractor in normal operating mode having a reel 30 for winding and holding the seat belt 20 thereon. A power source 41 in form of a linear actuator 33, such as a pneumatic or hydraulic actuator with stationary cylinder 35 and moveable piston 36, or a threaded electromechanical actuator (not showed) may be drivingly connected to the reel 30, which may be linearly displaced along a stationary guide 34 by means of the linear actuator 33. FIG. 4B shows the retractor in retracted operating mode, in which the reel 30 has been displaced by means of the linear actuator 33, thereby accomplishing powered retraction of the seat belt without rotation of the reel 30.

Consequently, the seat belt 20 associated with the vehicle seat 14 has a first attachment point 21 for fastening a waist portion 28 of the seat belt 20 to the seat 14 or vehicle chassis, and a second attachment point 22 for fastening a chest portion 29 of the seat belt 20 to the seat 14 or vehicle chassis, wherein the seat belt retractor 27 is located at the second attachment point 22 and configured for powered retraction or tensioning of the chest portion 29 of the seat belt 20, and wherein the second attachment point 22 is arranged: at the B-pillar 8 of the vehicle chassis, or at the floor 4 of the vehicle chassis, or at an interior side of the roof 5 of the vehicle chassis, or integrated in the vehicle seat 14, in particular in the backrest 14b or headrest 14c of the vehicle seat 14.

A first example embodiment of a vehicle seat system for moving an occupant of a vehicle seat to open airway position after a vehicle crash event is described below with reference to FIG. 5. The vehicle seat system comprises a seat 14 having a seat cushion 14a, a backrest 14b and a headrest 14c, wherein the seat 14 further has one or more power actuators 40 configured for adjusting a position of the backrest 14b and/or headrest 14c. The vehicle seat system further comprises a seat belt arrangement having a seat belt 20 and a seat belt retractor 27, wherein the seat belt arrangement further has power source 41 drivingly connected to the seat belt retractor 27 for enabling powered retraction. Moreover, the vehicle seat system comprises an electronic control system 42 operatively connected to the one or more power actuators 40 of the seat and power source 41 of the seat belt arrangement, wherein the control system 42 is configured for: determining occurrence of a vehicle crash event; and controlling operation of the one or more power actuators 40 of the seat 14 for moving at least a portion of the backrest 14b and/or headrest 14c backwards, and controlling operation of the power source 41 of the seat belt retractor 27 for pulling the occupant of the vehicle seat 14 backwards towards the backrest 14b.

Thereby, the occupant 18 of the vehicle seat 14 may be moved to open airway position in the event of vehicle crash.

The one or more power actuators 40 configured for adjusting a position of the backrest 14b and/or headrest 14c for moving the backrest 14b and/or headrest 14c rearwards may for example be electrical motors or linear actuators arranged within the seat 14 and drivingly connected to the backrest and/or headrest via suitable transmission mechanisms.

With reference to FIG. 7A, the vehicle seat 14 may for example include a first pivot shaft 43 located in an intersection region of the seat cushion 14a and backrest 14b and configured for enabling folding of the backrest 14b backwards, for example by means of an electrical motor or the like (not showed) drivingly connected to an adjustment mechanism coupled to the first pivot shaft 43 and/or backrest 14b for controlling folding position of the backrest 14b. The first pivot shaft 43 typically extends in the horizontal direction for enabling rearwards folding of the backrest 14b.

Figure 12:
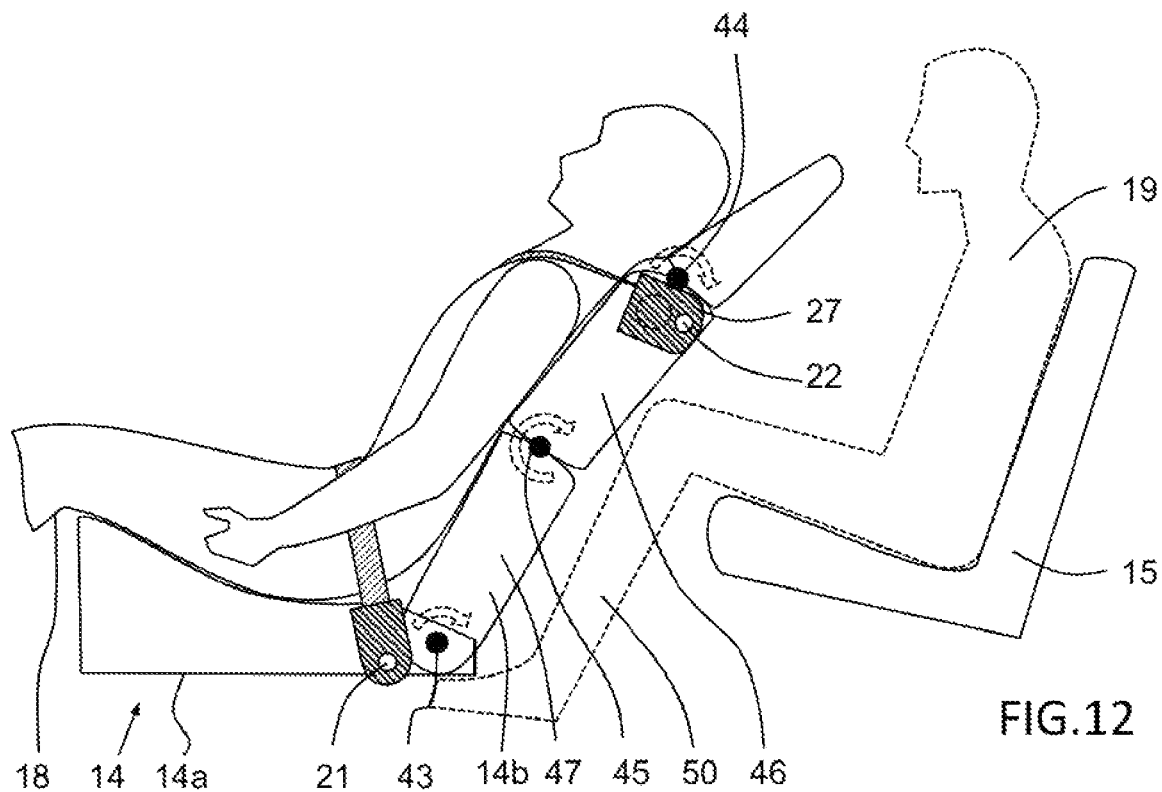
FIG. 12 shows schematically a seat having three pivot shafts according to the disclosure.

Moreover, with reference to FIG. 12, the vehicle seat 14 may for additionally include powered motion of the headrest 14c for moving the headrest 14c backwards. This backwards motion may for example be accomplished by pivoting the headrest backwards and/or sliding the headrest 4c backwards. Rearwards motion of both the backrest 14b and the headrest 14c may generally enable rearrangement of the body of the occupant to an even better position in terms of open airway due to the more rearwards inclined head position relative to the torso of the occupant.

On the example embodiment of FIG. 12, the vehicle seat 14 includes an upper pivot shaft 44 located in an intersection region of the backrest 14b and headrest 14c and configured for enabling folding of the headrest 14c backwards, for example by means of an electrical motor or the like (not showed) drivingly connected to an adjustment mechanism coupled to the upper pivot shaft 44 and/or headrest 14c for controlling folding position of the headrest 14c. The upper pivot shaft 44 may however alternatively be arranged within the backrest 14b. Still more alternatively, the vehicle seat 14 may include substantially horizontally oriented slide rails for enabling sliding motion of the headrest 14c backwards, for example by means of an electrical motor or the like drivingly connected to the headrest 14c.

Figure 11A:
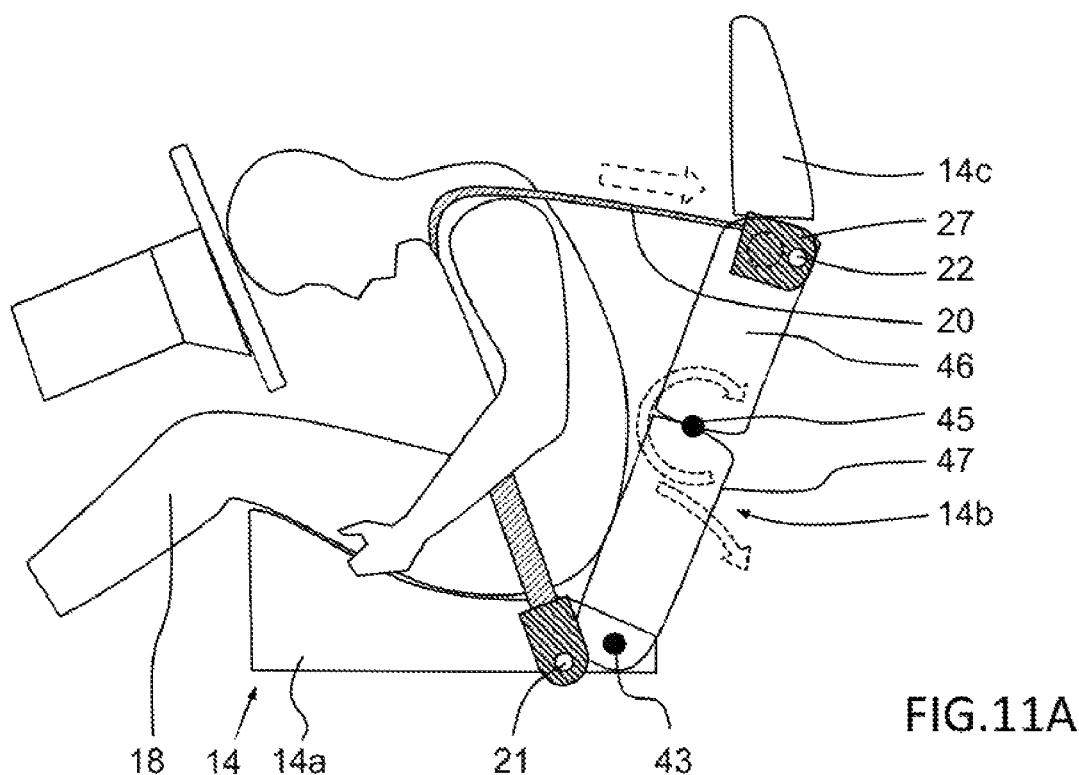
FIGS. 11A-11B show schematically two body postures and corresponding seat positions of yet another alternative embodiment of the seat and method for rearranging the occupant according to the disclosure.

Furthermore, with reference to FIG. 11A, the vehicle seat 14 may include a first pivot shaft located in the intersection region of the seat cushion 14a and backrest 14b and configured for enabling folding of the backrest 14b backwards, and a second pivot shaft 45 arranged in a region of the backrest 14b located between the first pivot shaft 43 and the headrest 14c and configured for enabling folding of an upper portion 46 of the backrest 14b located between the second pivot shaft 45 and headrest 14c backwards. The second pivot shaft 45 typically extends in the horizontal direction for enabling rearwards folding of the upper portion 46 of the backrest 14b relative to the lower portion 47 of the backrest 14b.

Partition of the backrest into a lower portion 47 and an upper portion 46 that are mutually pivotally connected for enabling rearwards motion of the upper portion 46 relative the lower portion 47 may generally enable rearrangement of the body of the occupant to a better position in terms of open airway due to the more rearwards inclined torso relative to an abdomen area of the occupant, and thus potentially also a more backwards tilted head position relative to body of the of the occupant.

Figure 11B:
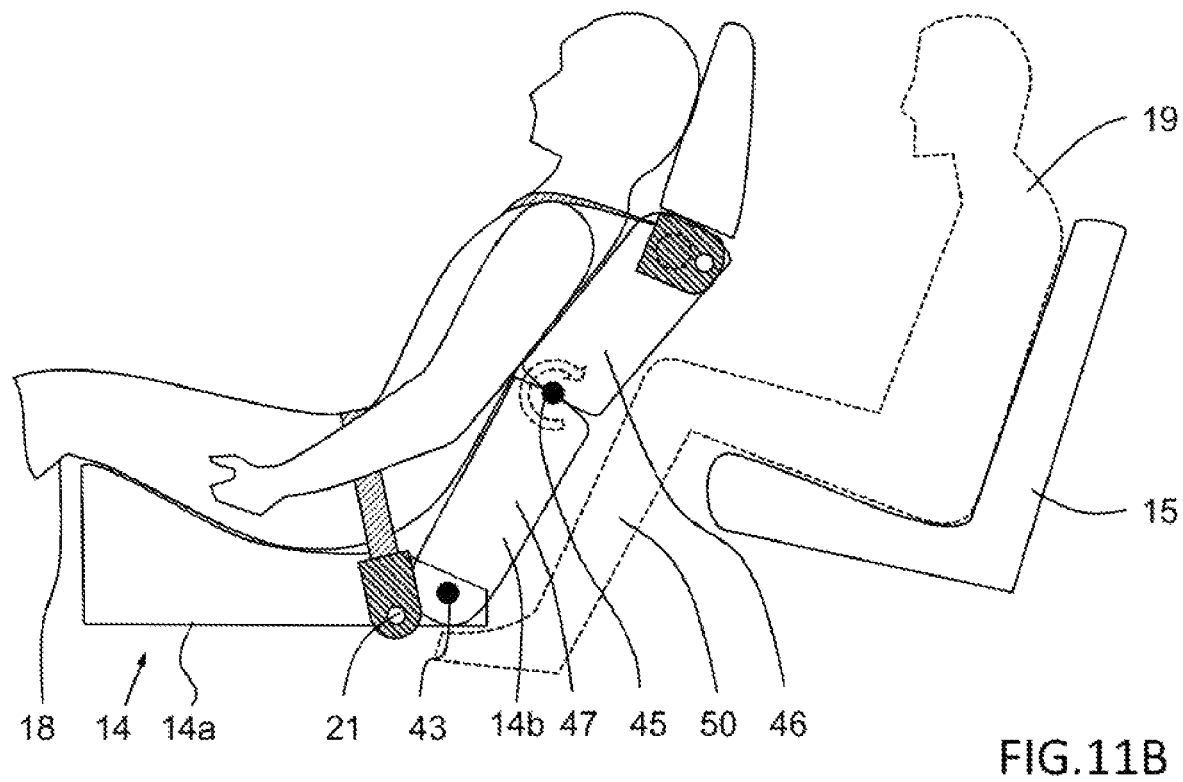

Furthermore, partition of the backrest into a lower portion 47 and an upper portion 46 at a second pivot shaft 45 also enables rearwards folding of the seat 14 while avoiding that the backrest 14b enters too much into the area of further occupant 19 sitting behind the seat 14, e.g. in a rear seat 15, as schematically showed in FIGS. 1 and 11B. Hence, the second pivot shaft 45 may assist in reducing the risk that the legs of a further occupant 19 sitting behind the occupant 18 are wedged by the backrest 14b.

Figure 13A:
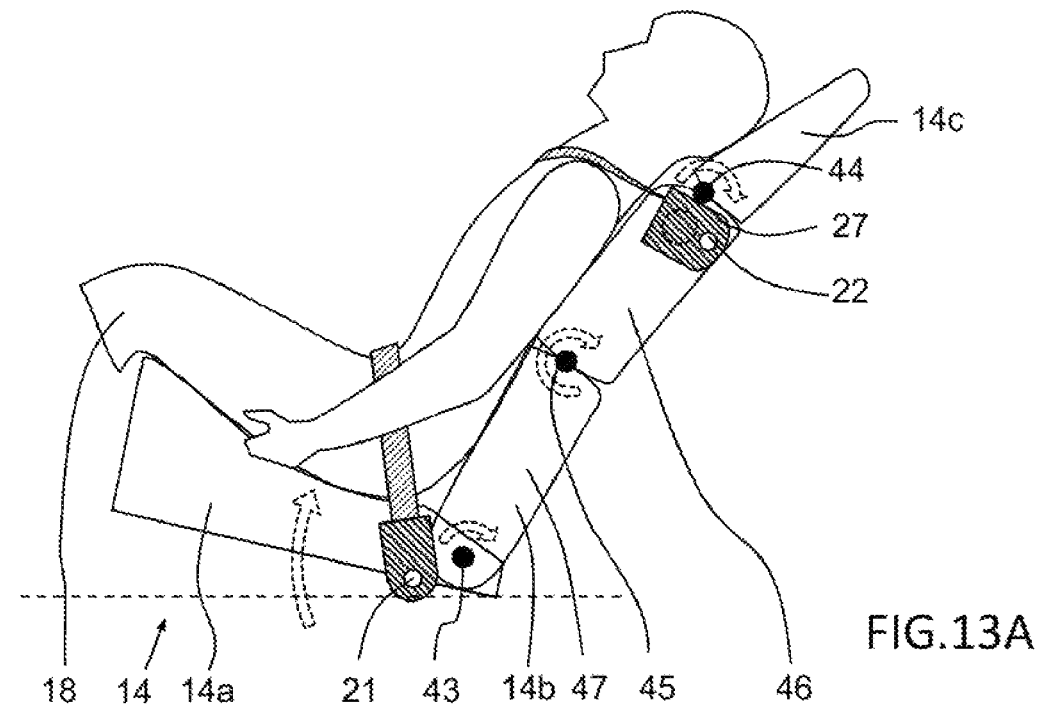
FIG. 13A shows schematically a seat having a rearwards tiltable seat cushion.

Moreover, with reference to FIG. 13A, the seat 14 may additionally be provided with a rearwards tiltable powered seat cushion 14a that may be controlled to tilt rearwards in connection with rearwards tilting of the backrest 14b. The seat cushion 14a may for example be tiltable around the first pivot shaft 43, or an another shaft located in an intersection region of the seat cushion 14a and backrest 14b.

A rearwards tilted seat cushion 14a may help keeping the body of the occupant 18 at a high position relative to the seat 14, such that the head of the occupant can better tilt rearwards together with a rearwards tiltable headrest 14c, and thus reducing the risk that the body of the occupant slides down relative to the seat 14 upon folding the backrest 14b rearwards. A more rearwards tilted head relative to the torso of the occupant generally enables improved open airways of the occupant 18.

The seat cushion 14a may be provided with a separate power function, such as electrical motor or linear actuator, for accomplishing the desired powered rearwards tilting motion of the seat cushion 14a. Alternatively, the seat cushion 14a and backrest 14b may form a unit that may be jointly rearward tilted, like a cradle, by means of a common power function.

Figure 13B:
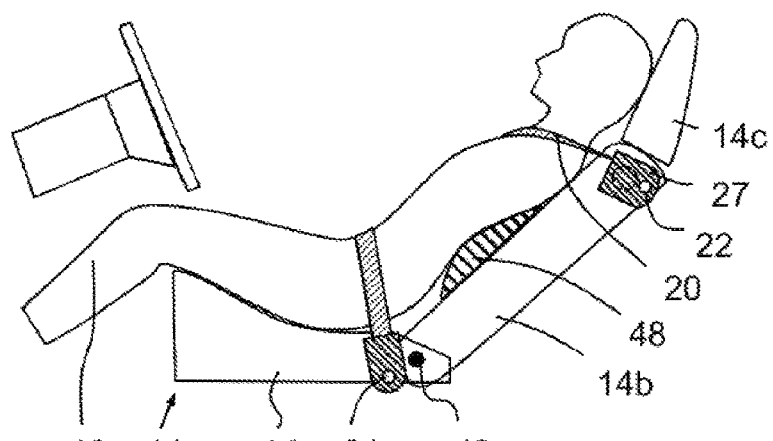
FIG. 13B shows schematically a seat having an adjustable lumbar support.

Furthermore, with reference to FIG. 13B, the vehicle seat 14 may include a lumbar support arrangement 48 or multi-contour arrangement for enabling further improved rearrangement of the body of the occupant to a better position in terms of open airway due to the more rearwards inclined torso relative to an abdomen area of the occupant. The adjustment of the lumbar support arrangement or multi-contour arrangement of the vehicle seat for protruding more towards a lumbar region and/or back region of the occupant of the vehicle seat may be powered using a dedicated power function, such as an electrical motor, a linear actuator, air pillows with associated air pump and air valve for controlling air pressure therein, etc.

Consequently, the seat 14 may be provided with various devices for enabling powered control of the seat position, and thus of the body posture of an occupant being seated in the seat, and any combination of devices of the seat 14 described above may be combined with each other in any combination. Hence, just as an example, the seat 14 may be provided with the first pivot shaft 43, and/or the second pivot shaft 45, and/or the upper pivot shaft 44 or sliding arrangement, and/or a lumbar support arrangement 48 or multi-contour arrangement, and/or the tiltable seat cushion 14a, or any combination thereof.

Figure 14:
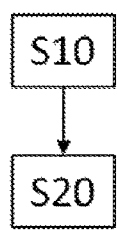
FIGS. 14-18 show schematically various alternative embodiments of the main steps of the method according to the disclosure.

The first example embodiment of the computer-implemented method for moving an occupant of a vehicle seat to open airway position after a vehicle crash event according to the disclosure will hereinafter be described with reference to FIGS. 7A-7D and FIG. 14. FIGS. 7A-7D shows the occupant 18 and associated seat position and seat belt status in four different time instances that correspond to before and after a vehicle crash, and FIG. 14 schematically shows the main steps of the method.

FIG. 7a schematically shows the body posture of the occupant 18 and position of the seat 14 and seat belt arrangement during normal driving, i.e. before a vehicle crash event. In this example embodiment, the first attachment point 21 is located at the floor 4 of the vehicle chassis and the second attachment point is arranged at a lower portion of the B-pillar 8 of the vehicle chassis. A seat belt guide 49 configured for guiding or deflecting the seat belt 20 is attached to an upper portion of the B-pillar 8, such that the seat belt is routed from the seat belt retractor 27 to the occupant 18 via the seat belt guide 49.

The method comprises a first step S10 of detecting occurrence of a vehicle crash event. This may for example be performed by monitoring vehicle acceleration level and detecting occurrence of a vehicle crash event when monitored vehicle acceleration level exceeds a threshold value. Specifically, the seat system may include an acceleration sensor, or a plurality of acceleration sensors being installed to be sensitive to acceleration levels in different directions, wherein the control system 42 is configured for detecting occurrence of a vehicle crash event by monitoring vehicle acceleration level by means of the vehicle acceleration sensor and detecting occurrence of a vehicle crash event when monitored vehicle acceleration level exceeds a threshold value.

The step of detecting occurrence of a vehicle crash event may alternatively be performed by monitoring, or receiving information about, deployment of an airbag within the vehicle. The vehicle airbags typically has internal acceleration sensors and deployment of an airbag within the vehicle may be a relatively reliable indication of the occurrence of a vehicle crash event.

The first step S10 of detecting occurrence of a vehicle crash event thus corresponds to detecting occurrence of a real vehicle crash event, i.e. detecting an ongoing vehicle crash event. In other words, detecting occurrence of a vehicle crash event does not correspond to merely determination of an imminent vehicle crash event, i.e. determination of a future vehicle crash event that has not yet started but which is estimated about to happen in a very near future, such as for example within the coming five seconds or less, or the like.

Figure 7B:
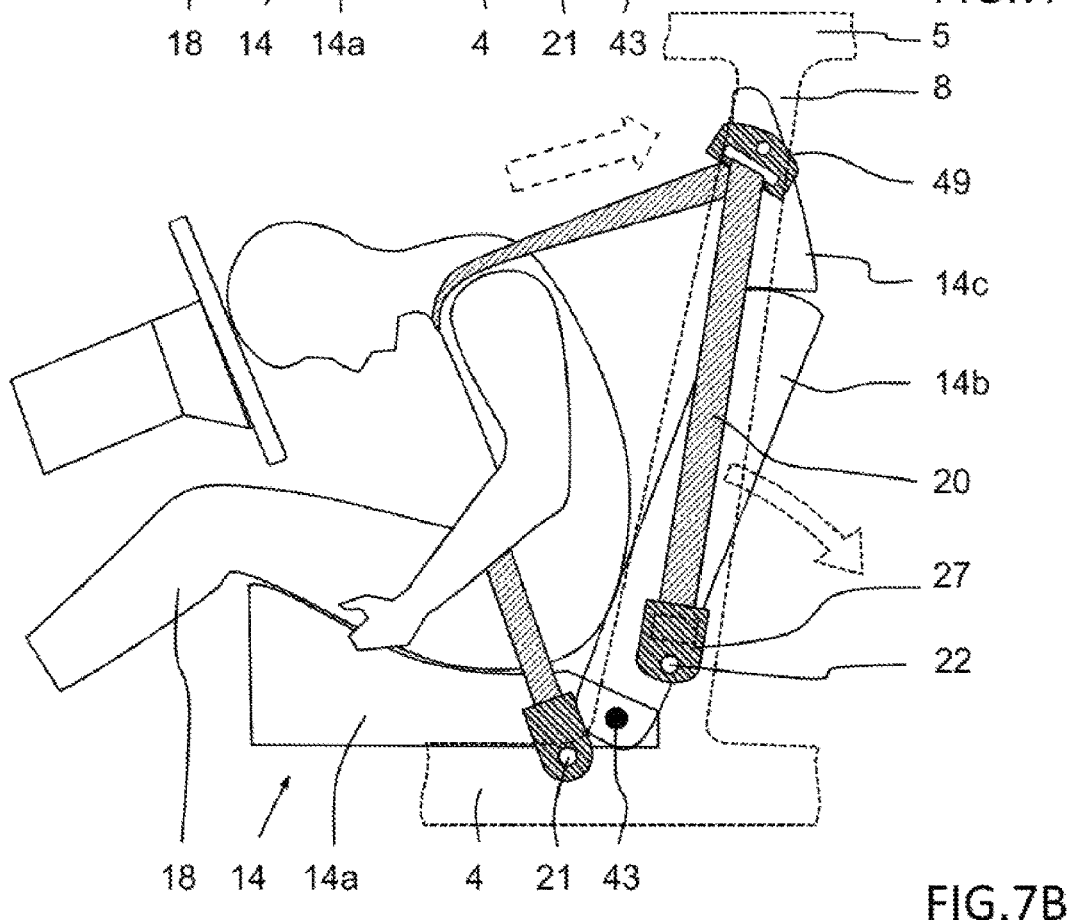

As a consequence of the vehicle crash event, the occupant may become unconscious in a body posture that results in hindered airway, i.e. hindered air passage between the occupant's lungs and mouth and/or nose. For example, the head of the occupant may be strongly forward leaning while the torso in still relatively upright sitting, or the head of the occupant may be strongly forward leaning in combination with a forward leaning torso, as schematically illustrated in FIG. 7B. In such a seating position, the airway passage in the throat region of the occupant may be restricted or even blocked.

Consequently, with reference again to FIG. 14, the method comprises a second step S20 of moving at least a portion of the backrest and/or headrest backwards and pulling an occupant of the vehicle seat backwards towards the backrest by powered retraction of a seat belt of the occupant by means of a seat belt retractor.

Figure 7C:
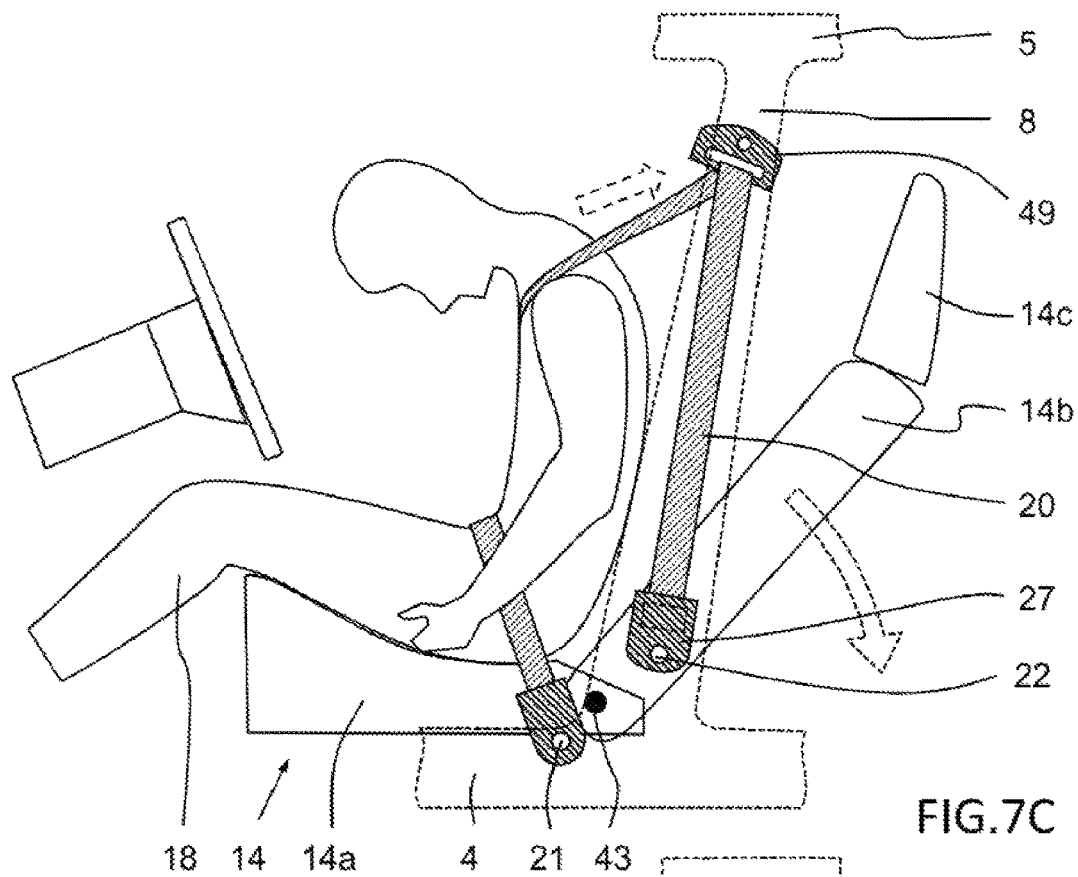
Figure 7D:
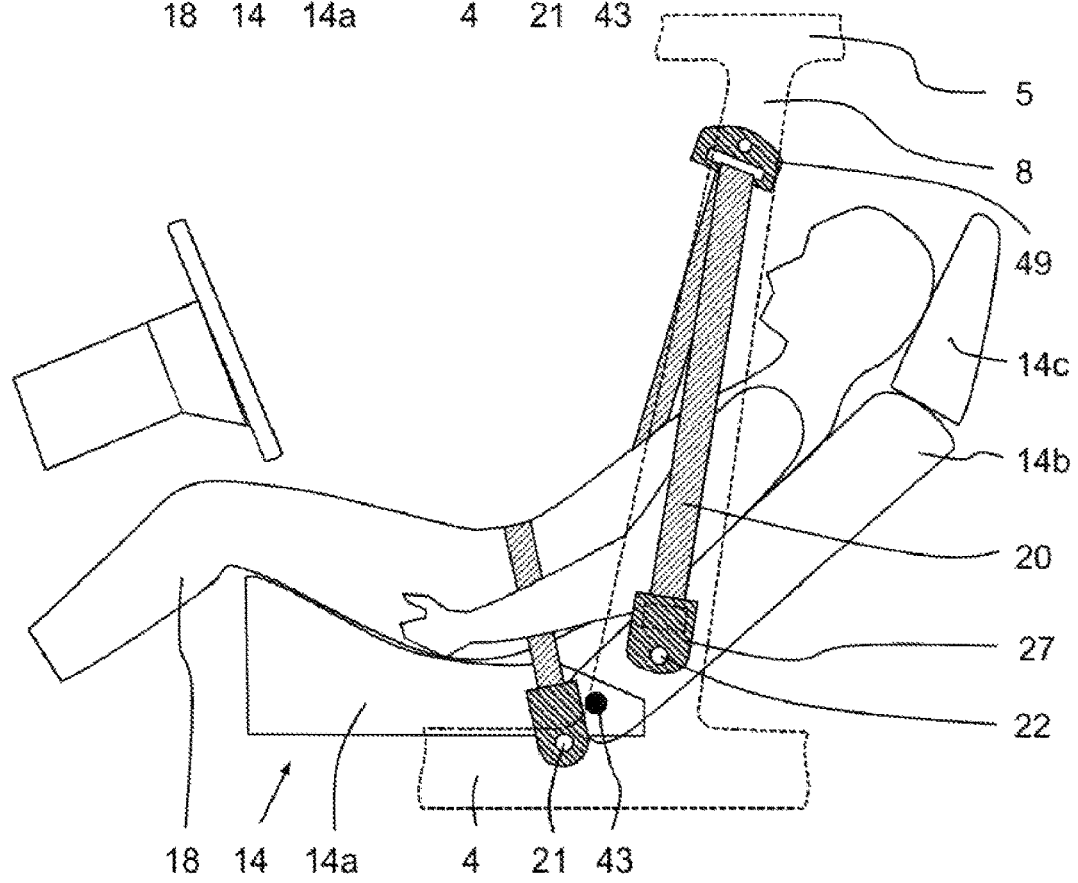

Thereby, the occupant of the vehicle seat may be moved to open airway position, as schematically illustrated in FIG. 7D, i.e. a position in which the likelihood of an open airway passage is higher than in the position before the occupant was moved backwards by means of the seat and seat belt arrangement.

The second step S20 of moving at least a portion of the backrest and/or headrest backwards and pulling an occupant of the vehicle seat backwards towards the backrest by powered retraction of a seat belt of the occupant by means of a seat belt retractor is initiated first after said first step S10 of detecting occurrence of a vehicle crash event has occurred.

The step of moving at least a portion of the backrest 14b and/or headrest 14c backwards preferably involves either moving at least a portion of the backrest 14b backwards, or moving both the backrest 14b and headrest 14c backwards. Moving only the headrest 14c appears in most cases insufficient, but may nevertheless be sufficient in certain implementations and situations, depending on the circumstances. In the example embodiment illustrated in FIGS. 7B-7D, only the backrest 14b is moved backwards, while the headrest 14c remains stationery with respect to the backrest 14b. Specifically, the backrest 14b is folded backwards around the first pivot shaft 43 located in an intersection region of the seat cushion 14 and backrest 14b.

Movement of the headrest 14c backwards should herein be interpreted as being moved separately relative to the backrest 14b, or separately relative to a portion of the backrest. Hence, movement of the headrest 14c backwards merely caused by folding of the backrest 14b is not deemed being movement of the headrest 14c relative to the backrest 14b. In other words, movement of at least a portion of the backrest 14b and the headrest 14c backwards involves two individual motions that may be performed simultaneously or consecutively.

Moreover, moving at least a portion of the backrest and/or headrest backwards may be performed by means of one or more power actuators 40 configured for adjusting a position of the backrest 14b and/or headrest 14c, as described above with reference to FIG. 5.

Reclining of the seat 14, i.e. moving the backrest rearwards by folding the backrest 14b backwards, or tipping the entire seat 14 including seat cushion 14a, backrest 14b and headrest 14c backwards, may in certain situations be sufficient for causing the occupant to change body posture to a more rearwards leaning and laid back body posture. However, in certain situations, merely moving the backrest 14b rearwards will not be sufficient for moving for example an unconscious occupant of the vehicle seat 14 to a more open airway position.

Consequently, for avoiding that the torso and head of the occupant nevertheless remains in a forward leaning body posture, the seat belt may be used for pulling the occupant rearwards. Hence, a combined action of leaning the seat backrest 14b and pulling the occupant rearwards towards the backrest 14b by powered retraction of the seat belt 29 may be required for moving the occupant rearwards to become seated in a more relaxing and reclined seating position with the head resting against the headrest, as depicted by FIG. 7D, thereby reducing the risk for respiration problems caused by hindered or even blocked airway.

With reference to FIGS. 7B-7D, the step of moving at least a portion of the backrest 14b and/or headrest 14c backwards and pulling an occupant 18 of the vehicle seat 14 backwards towards the backrest 14b by powered retraction of the seat belt 29, from the start position in FIG. 7A to the end or final position in FIG. 7D, may be performed simultaneously and/or consecutively. In other words, the backrest 14b and/or headrest 14c may be moved backwards while the occupant 18 simultaneously is pulled backwards towards the backrest 14b by powered retraction of the seat belt 29. Alternatively, the method may include a first phase in which the backrest 14b and/or headrest 14c is moved backwards while the seat belt retractor 27 remains inactive, and a second phase in which the backrest 14b and/or headrest 14c remains stationary while the seat belt retractor 27 is actively retracting seat belt 29.

The control system 42 may have a predetermined operation routine stored on a data memory for controlling the power source 41 of the seat belt retractor 27 and the one or more power actuators 40 for adjusting a position of the backrest 14b and/or headrest 14c. For example, the step of moving at least a portion of the backrest and/or headrest backwards and pulling an occupant of the vehicle seat backwards towards the backrest by powered retraction of the seat belt may be performed by, during a first half of the motion sequence, primarily pulling the occupant 18 of the vehicle seat 14 backwards towards the backrest 14b by powered retraction of the seat belt 29 while keeping the backrest 14b and/or headrest 14c relatively stationary, and subsequently during a second half of the motion sequence, primarily moving at least a portion of the backrest 14b and/or headrest 14c backwards while ensuring that the occupant remains in close contact with, or adjacent to, the backrest 14b and/or headrest 14c.

In implementations where the seat belt retractor is fastened to the vehicle chassis, a certain retraction, i.e. pulling in, of the seat belt 29 is necessary while folding or moving the backrest 14b rearwards for ensuring that the occupant remains in close contact with, or adjacent to, the backrest 14b and/or headrest 14c. However, in implementations where the seat belt retractor is fastened to the backrest 14b or headrest 14c, no further retraction of the seat belt 29 is necessary when having arrived at a state in which the occupant is in close contact with, or adjacent to, the backrest 14b and/or headrest 14c.

The control system 42 may have one or more predetermined operation routines stored for controlling the power source 41 of the seat belt retractor 27 and the one or more power actuators 40 for adjusting a position of the backrest 14b and/or headrest 14c. If a plurality of predetermined operation routines is available, the control system 42 may select the appropriate operation routine based on the specific circumstances. In other words, the control system 42 may obtain some type of data input reflecting the specific circumstances and subsequently selecting an appropriate operation routine based on said data input.

For example, the control system may obtain data input from a body posture sensor, such as an image detector 17, ultrasonic transducer, laser scanner, or the like, arranged within the passenger compartment of the vehicle. Moreover, the control system 42 may even include a dynamic operation routine that continuously adapts its operation according to the dynamic input data provided by said body posture sensor, and based in data input reflecting the position of the backrest 14b and/or headrest 14c.

If the seat belt arrangement associated with the seat includes multiple seat belt retractors, such as for example a four or five point seat belt with one seat belt retractor at each upper side of the seat, the control system 42 may be configured to control each seat belt retractor individually, either according to one or more predetermined operation routines, or by applying a dynamic operation routine that continuously adapts its operation according to obtained dynamic input data.

The overall aim is generally to operate and control the power source 41 of the seat belt retractor 27 and the one or more power actuators 40 for adjusting a position of the backrest 14b and/or headrest 14c, such that the occupant is moved rearwards to become seated in a more relaxing and reclined seating position with the head resting against the headrest in a smooth and relatively slow manner without exerting excessive pressure on the chest of the occupant by means of the seat belt 29 and while avoiding that the occupant falls uncontrolled rearwards.

Figure 8A:
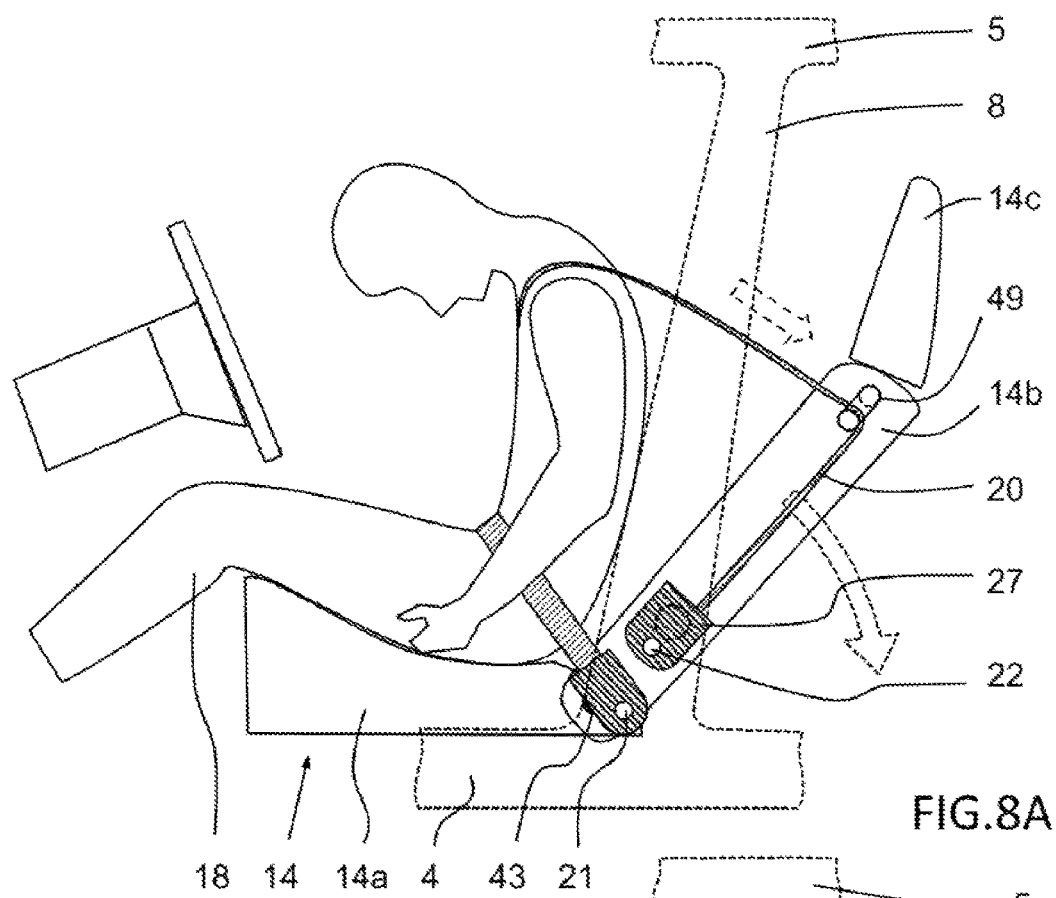
FIGS. 8A-8B show schematically two body postures and corresponding seat positions of an alternative embodiment of the seat and method for rearranging the occupant according to the disclosure.
Figure 8B:
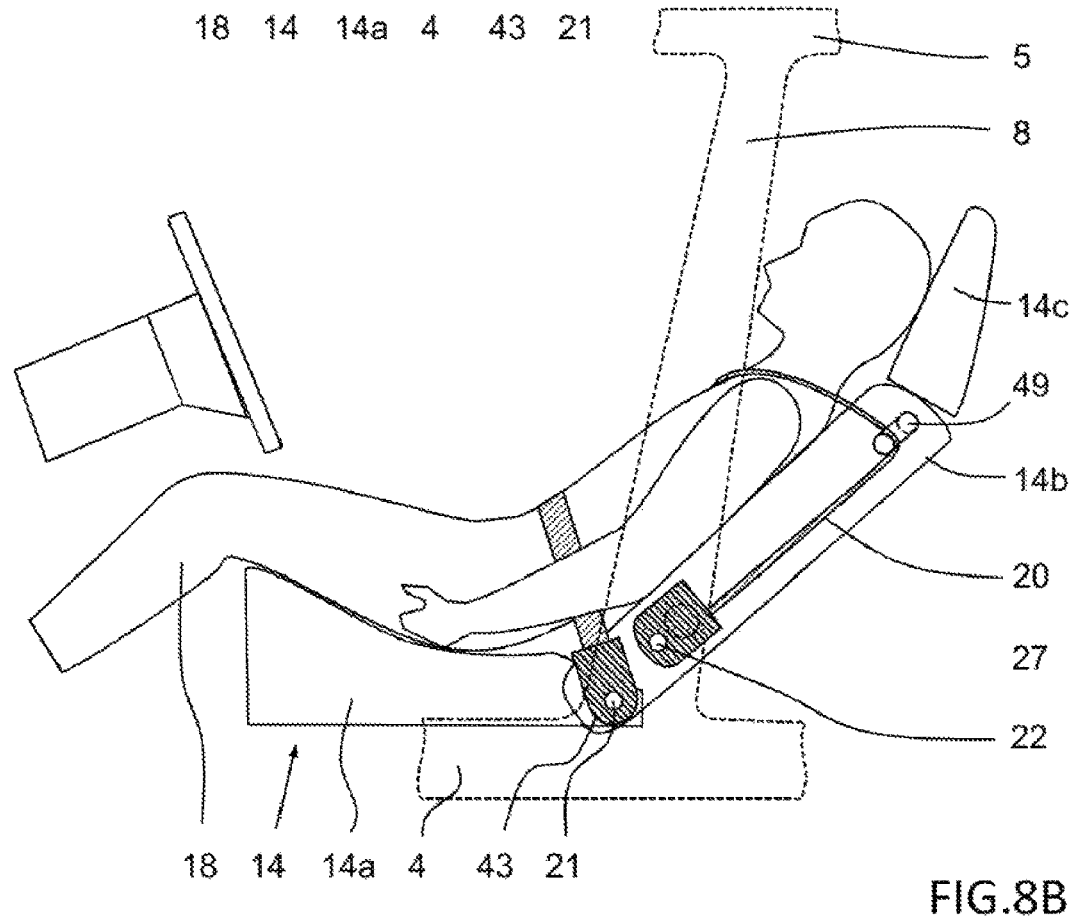

FIGS. 8A and 8B schematically shows the body posture of the occupant 18 and position of the seat 14 and seat belt arrangement in an intermediate position and a final position, respectively, for a further example embodiment of the seat and seat belt arrangement. In this example embodiment, the backrest is foldable around a first pivot shaft 43. The first attachment point 21 is located at the floor 4 of the vehicle chassis and the second attachment point 22 is arranged at a lower portion of the B-pillar 8 of the vehicle chassis.

The backrest 14b comprises a seat belt guide 49 configured for guiding or deflecting the chest portion of the seat belt 29 along its path towards the seat belt retractor 27. As a result, the seat belt 29 may exert an effective pull-back effect on the occupant irrespective of backrest folding position, thereby enabling a better control of the body posture of the occupant while moving the backrest 14b backwards.

Figure 9A:
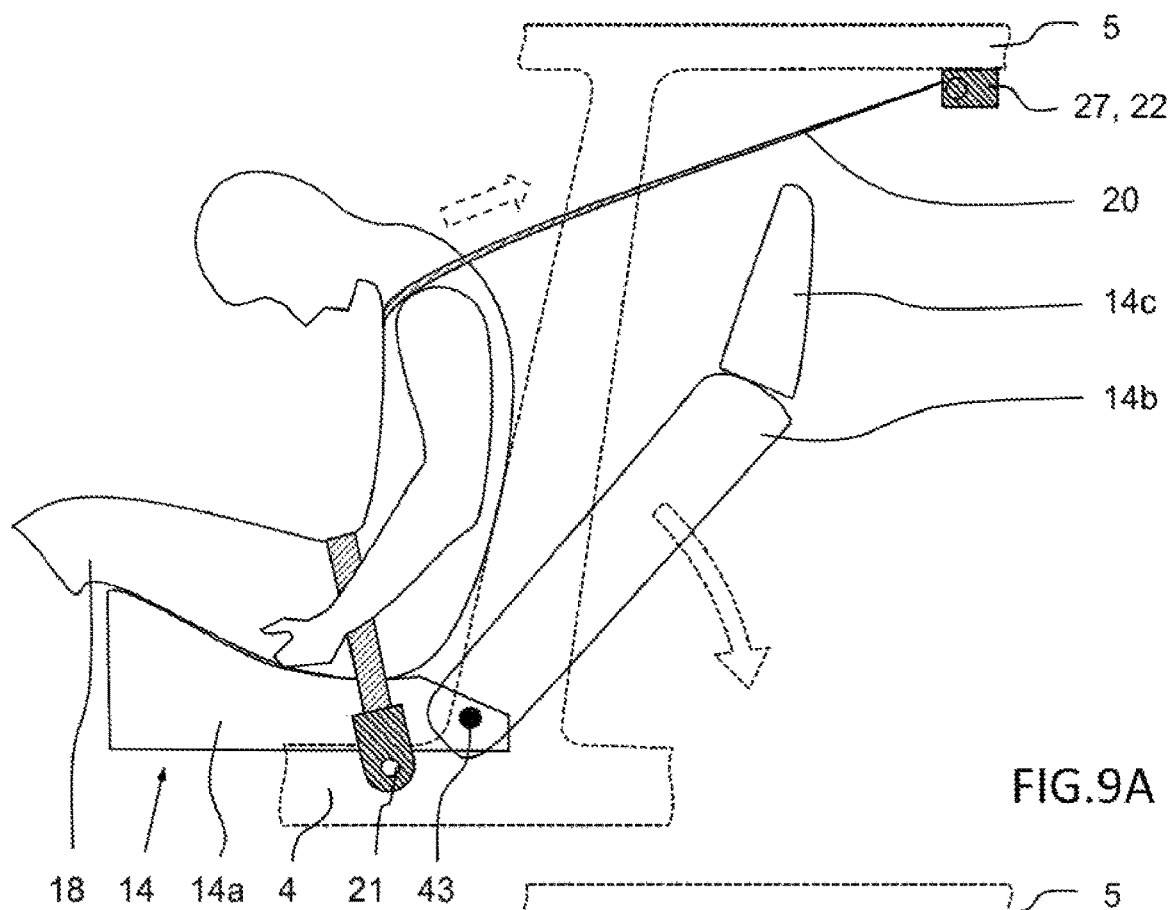
FIGS. 9A-9B show schematically two body postures and corresponding seat positions of a further alternative embodiment of the seat and method for rearranging the occupant according to the disclosure.
Figure 9B:
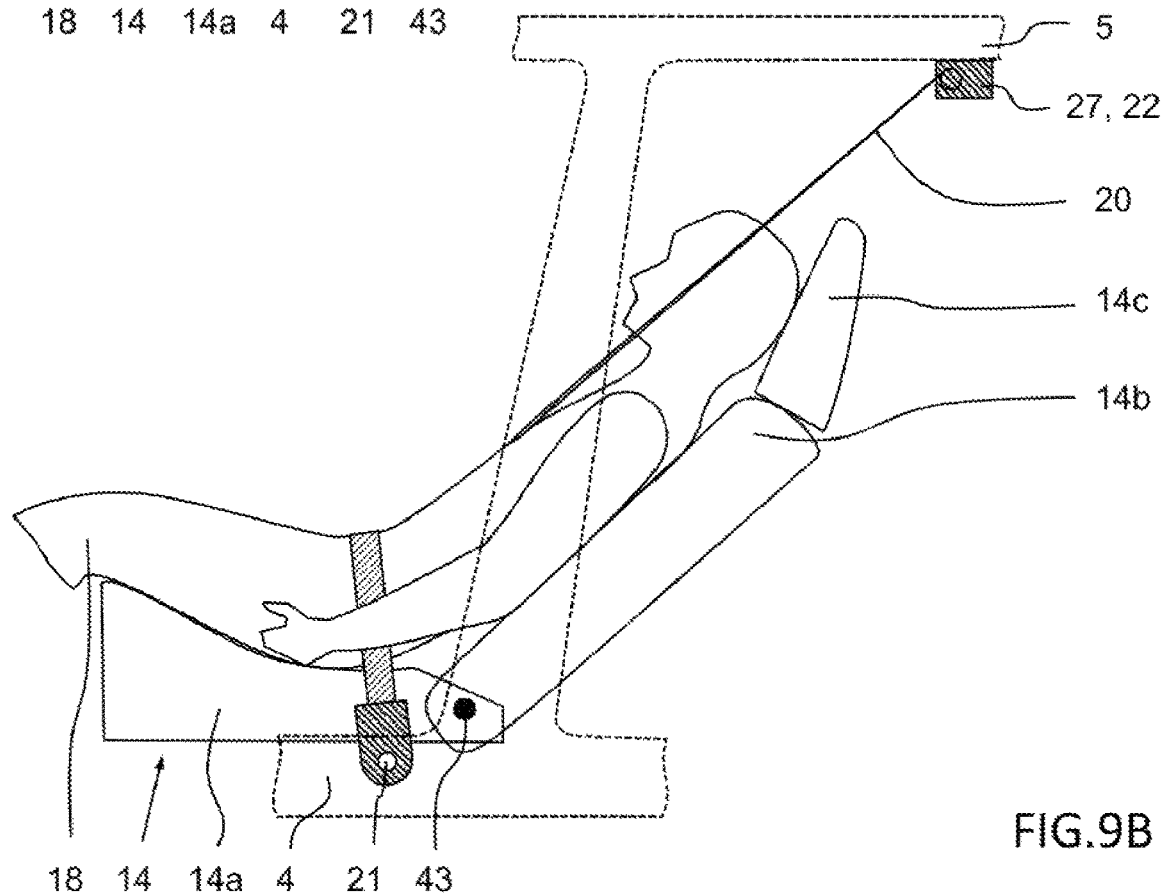

FIGS. 9A and 9B schematically shows the body posture of the occupant 18 and position of the seat 14 and seat belt arrangement in an intermediate position and a final position, respectively, for a further example embodiment of the seat and seat belt arrangement. In this example embodiment, the backrest is foldable around a first pivot shaft 43 and the first attachment point 21 is located at the floor 4 of the vehicle chassis. However, in this example embodiment, the second attachment point 22 is arranged at an interior side of the roof 5 of the vehicle chassis. Having the second attachment point 22 at the roof 5 may for example be advantageous for the centre position of the rear bench of the vehicle, or the like, because this position has no nearby B-pillar or C-pillar of the chassis.

Figure 10A:
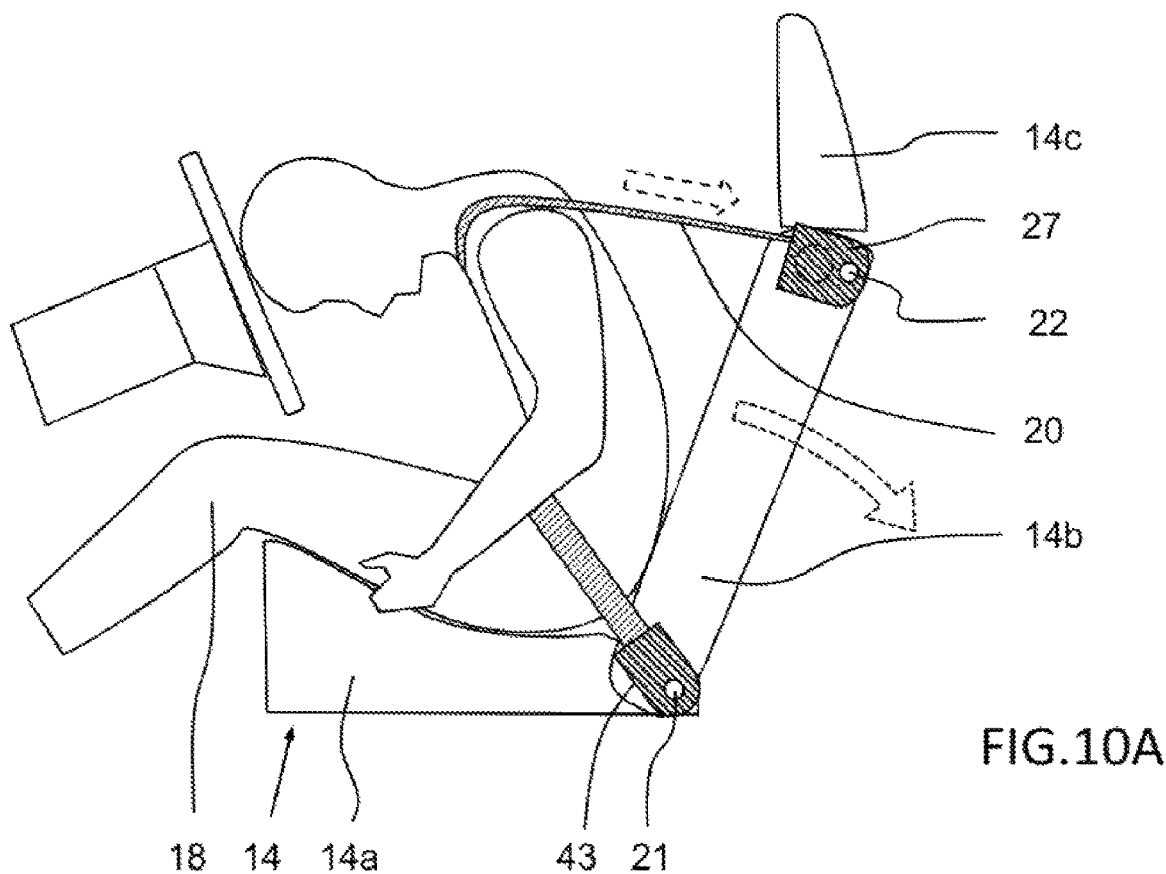
FIGS. 10A-10B show schematically two body postures and corresponding seat positions of still a further alternative embodiment of the seat and method for rearranging the occupant according to the disclosure.
Figure 10B:
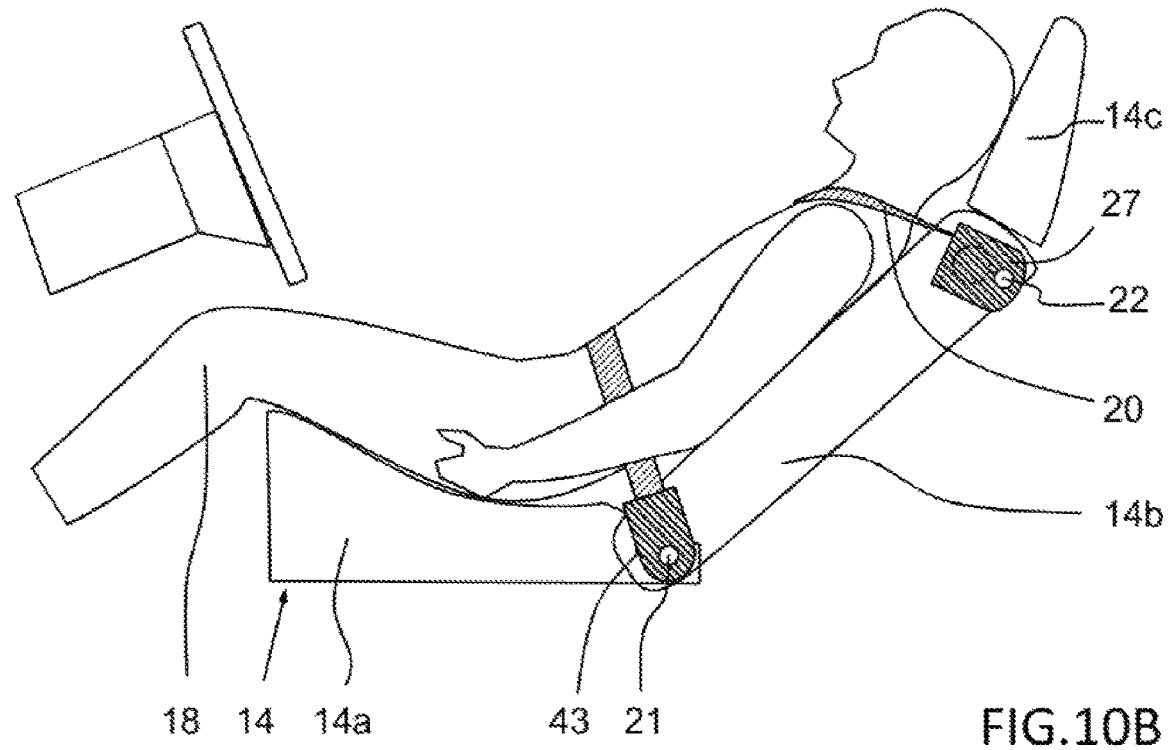

FIGS. 10A and 10B schematically shows the body posture of the occupant 18 and position of the seat 14 and seat belt arrangement in a start position and a final position, respectively, for a further example embodiment of the seat and seat belt arrangement. In this example embodiment, the backrest is foldable around a first pivot shaft 43. Moreover, the second attachment point 22 is arranged integrated in the vehicle seat, in particular in the backrest 14b of the vehicle seat 14. Having the second attachment point 22 on the backrest 14b is advantageous in that the seat belt 29 may exert an effective pull-back effect on the occupant irrespective of backrest folding position, thereby enabling a better control of the body posture of the occupant while moving the backrest 14b backwards, while also eliminating the need for a seat belt guide 49 as illustrated in FIG. 8a. Moreover, this arrangement of the second attachment point 22 is also beneficial for cabriolet vehicles or other types of vehicles lacking an nearby B- or C-pillar that may be used for the second attachment point 22.

FIGS. 11A and 11B schematically shows the body posture of the occupant 18 and position of the seat 14 and seat belt arrangement in a start position and a final position, respectively, for a further example embodiment of the seat and seat belt arrangement. In this example embodiment, the backrest 14b is foldable around the first pivot shaft 43. The backrest further includes a second pivot shaft 45 arranged in a region between the first pivot shaft 43 and the headrest 14c, wherein the step of moving at least a portion of the backrest 14b and/or headrest 14c backwards additionally involves folding the backrest 14b backwards around the second pivot shaft 45.

By providing the backrest 14b with an additional folding arrangement that divides the backrest 14b in lower and upper portions 47, 46, the torso and head of the occupant may have a larger backwards inclination without necessarily folding the lower portion 47 of the backrest 14b equally much as a backrest without the additional folding arrangement. As a result, the space left for the legs 50 of a further occupant 19 seated in a backseat of the vehicle 1 may be larger. In other words, the additional folding arrangement, i.e. the second pivot shaft 45, enables larger backwards inclined torso and head position, and thus increased likelihood that thee head of the occupant will actually rest against the headrest 14c in the final position, and also a more open airway due to the more backwards curved upper body of the occupant.

FIG. 12 shows a further example embodiment of the seat system, with the body posture of the occupant 18 and position of the seat 14 and seat belt arrangement in the final position, similar to the embodiment of FIG. 11B, but here additionally including an upper pivot shaft 44 located in an intersection region of the backrest 14b and headrest 14c and configured for enabling folding of the headrest 14c backwards. In general, a more backwards tilted head position relative to body of the of the occupant enables improved open airway and reduced risk for respiration problems, compared with a non-rearwards tilted head position.

Moreover, by providing also a backwards foldable or moveable headrest 14c, the head of the occupant may have an even larger backwards inclination without necessarily folding the upper portion 46 of the backrest 14b equally much as an upper portion 46 of the backrest without the upper pivot shaft 44. As a result, the space left for the legs 50 of a further occupant 19 seated in a backseat of the vehicle 1 may be larger. In other words, the upper pivot shaft 44 enables larger backwards inclined head position, and thus increased likelihood that thee head of the occupant will actually rest against the headrest 14c in the final position, and also a more open airway due to the more backwards curved upper body of the occupant.

According to a further alternative embodiment, the backwards foldable or moveable headrest 14c, implemented for example by means of upper pivot shaft 44, may be combined with the non-divided backrest 14*c*, i.e. a backrest 14*b* without the additional folding arrangement of the backrest 14*b* implemented for example by means of the second pivot shaft 45.

Consequently, the step of moving at least a portion of the backrest and/or headrest backwards may involve performing one, two, three, or all of the following activities: folding the backrest backwards around a first pivot shaft located in an intersection region of the seat cushion and backrest, moving the headrest 14*c* backwards, tilting the seat cushion 14*a* backwards, adjusting a lumbar support arrangement 48 or multi-contour arrangement of the vehicle seat for protruding more towards a lumbar region and/or back region of the occupant of the vehicle seat.

Figure 15:
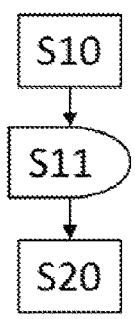

The second step S20 of moving the backrest 14*b* backwards and pulling the occupant backwards is preferably performed first after the vehicle crash event, i.e. after the crash event has ended. In other words, the second step S20 is preferably performed first when the vehicle has come to stillstand directly after a crash event, and not interfering with the position or control of the seat and/or seat belt arrangement during the crash event. Consequently, with reference to FIG. 15, the method may comprises an intermediate step S11 of waiting a certain time period after the first step S10 of detecting occurrence of a vehicle crash event, and before the second step S20 of moving at least a portion of the backrest and/or headrest backwards and pulling an occupant of the vehicle seat backwards towards the backrest.

The intermediate step S11 of waiting a certain time period may for example involve performing a delay for a time period of at least 3 seconds, specifically at least 5 seconds. Alternatively, the delay time period may be within a range of 3-30 seconds, specifically within a range of 5-15 seconds.

Furthermore, according to some example embodiments, it may be desirable to perform some type of checking process for evaluating the need for a change of body posture of the occupant before performing the second step S20 of moving at least a portion of the backrest and/or headrest backwards and pulling an occupant of the vehicle seat backwards towards the backrest. In other words, it may be desirable to avoid an automatic motion of at least a portion of the backrest and/or headrest backwards and automatic pulling of the occupant of the vehicle seat backwards towards the backrest in situations when there is no need for such change of body posture, or even is undesirable. For example when the occupant is not unconscious or the respiration activity is not hindered or blocked.

Figure 16:
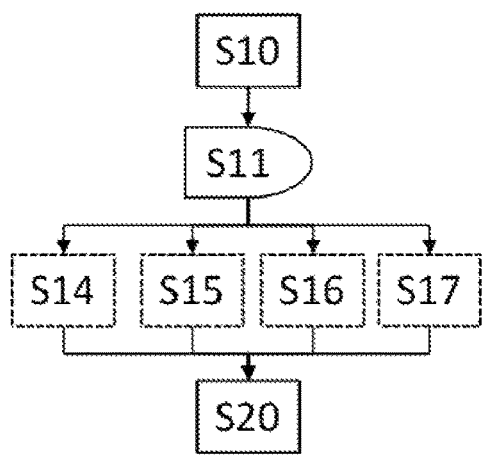

Therefore, with reference to FIG. 16, the method may comprise a first intermediate step S14 of obtaining information about airway status of the occupant, and progressing to said second step S20 of moving at least a portion of the backrest and/or headrest backwards and pulling an occupant of the vehicle seat backwards towards the backrest when the detected airway status indicates blocked or hindered airway of the occupant. Hence, in those instances when the obtained information about the airway status indicates non-blocked or non-hindered airway, the method does not progress to said second step S20.

The information about airway status that may be used for providing an indication of blocked or hindered airway of the occupant, may for example correspond to monitoring of breathing activity of the occupant, for example by monitoring body breathing motion using an image detector 17, ultrasonic transducer, laser scanner, etc., or by audio detection using a microphone 51, as schematically illustrated in the system according to FIG. 6.

Alternatively, said information about airway status that may be used for providing an indication of blocked or hindered airway of the occupant may for example correspond to a voice command detected by means of the microphone 51 and given by the occupant in response to a question generated by the control system 42 and posed by a loudspeaker 53 within the passenger compartment the system. In other words, the control system 42 may ask the occupant about the health status and respiratory status and register a voice response given by the occupant, and subsequently derive therefrom whether response indicates blocked or hindered airway of the occupant.

Alternatively, or in combination with the first intermediate step S14, the method may comprise a second intermediate step S15 of obtaining information about a level of consciousness of the occupant, and progressing to said second step S20 of moving at least a portion of the backrest and/or headrest backwards and pulling an occupant of the vehicle seat backwards towards the backrest when the detected level of consciousness of the occupant is low or non-existing, i.e. an unconscious occupant. Hence, in those instances when the obtained information about the level of consciousness of the occupant is high or at least medium, the method does not progress to said second step S20.

Said information about the level of consciousness of the occupant may for example correspond to a voice response detected by means of the microphone 51 and given by the occupant in response to a question generated by the control system 42 and posed by a loudspeaker 53 within the passenger compartment the system. In other words, the control system 42 may ask the occupant about the health status and consciousness level of the occupant and register a voice response given by the occupant, and subsequently derive therefrom a level of consciousness of the occupant.

Alternatively, information about a level of consciousness of the occupant may correspond to a level of physical activity or motion of the occupant, as for example detected by means of an image detector 17, ultrasonic transducer, laser scanner, etc. Physical activity or motion of the occupant indicates that the occupant may be used as indication that occupant is conscious.

Alternatively, or in combination with any of the first and second intermediate steps S14, S15, the method may comprise a third intermediate step S16 of obtaining information about values of one or more health parameters associated with the respiratory and/or cardiovascular systems of the occupant, and progressing to said second step S20 of moving at least a portion of the backrest and/or headrest backwards and pulling an occupant of the vehicle seat backwards towards the backrest when the detected values of the one or more health parameters is outside of a predetermined range. Hence, in those instances when the obtained information about the about values of one or more health parameters is within the ranges of acceptable values, the method does not progress to said second step S20.

With reference to FIG. 6, the one or more health parameters associated with the respiratory and/or cardiovascular systems of the occupant may for example be blood oxygen saturation (SPO2) as measured using for example an oximeter 52*a*, which may be included in smart watch. A low oxygen saturation may be used as indication of blocked or hindered airway.

Alternatively, the one or more health parameters associated with the respiratory and/or cardiovascular systems of the occupant may for example be electrocardiogram (ECG), or similar heart activity monitoring parameter, as measured using for example electrodes 52*b*, which may be included in smart watch. A heart activity outside of normal activity may be used as indication of blocked or hindered airway.

Alternatively, the one or more health parameters associated with the respiratory and/or cardiovascular systems of the occupant may for example be number of heart beats per minute (BPM), or similar heart activity monitoring parameter, as measured using for example optical sensor 52c, which may be included in smart watch. A heart beat rate outside of normal heart beat rates may be used as indication of blocked or hindered airway.

Alternatively, the one or more health parameters associated with the respiratory and/or cardiovascular systems of the occupant may for example be blood pressure (BP), or similar heart activity monitoring parameter, as measured using for example optical sensors 52d, which may be included in smart watch. A blood pressure outside of normal blood pressure levels may be used as indication of blocked or hindered airway.

Alternatively, or in combination with any of the first, second and third intermediate steps S14-S16, the method may comprise a fourth intermediate step S17 of obtaining information about body posture of the occupant, and progressing to said second step S20 of moving at least a portion of the backrest and/or headrest backwards and pulling an occupant of the vehicle seat backwards towards the backrest when the detected body posture indicates blocked airway. Hence, in those instances when the obtained information about the about body posture indicates non-blocked or non-hindered airway, the method does not progress to said second step S20. The body posture may for example detected by means of an image detector 17, ultrasonic transducer, laser scanner, etc.

Clearly, although not explicitly shown in FIG. 16, only one of the first to fourth intermediate steps S14-S17 may be implemented in isolation from the others for providing an indication of blocked or hindered airway of the occupant. Moreover, two, three or all of the first to fourth intermediate steps S14-S17 may be combined in any order to provide a more reliable indication of blocked or hindered airway of the occupant.

In addition, any obtained data and/or information about airway status of the occupant, the level of consciousness of the occupant, values of one or more health parameters associated with the respiratory and/or cardiovascular systems of the occupant, and/or body posture of the occupant, as detected and registered by appropriate sensors as described above with reference to FIG. 16, may be automatically forwarded to an emergency call centre and/or ambulance crew for enabling an emergency call centre and/or ambulance crew to make better decisions about level of urgency and/or for enabling better preparation before arriving at the crash site.

Moreover, occupant information about airway status, level of consciousness, values of one or more health parameters, and/or body posture may also be obtained after the second step S20 of moving at least a portion of the backrest 14b and/or headrest 14c backwards and pulling an occupant of the vehicle seat 14 backwards towards the backrest 14b, and then automatically forwarded to the emergency call centre and/or ambulance crew. Thereby, the emergency call centre and/or ambulance crew can evaluate whether the seat motion for rearranging the occupant to a more open airway position was actually effective or not, and make better decisions based thereon.

With respect to the second step S20 involving moving at least a portion of the backrest and/or headrest backwards, said motion of at least a portion of the backrest and/or headrest backwards may be continued until arriving at a predetermined reclined seat position.

Figure 17:
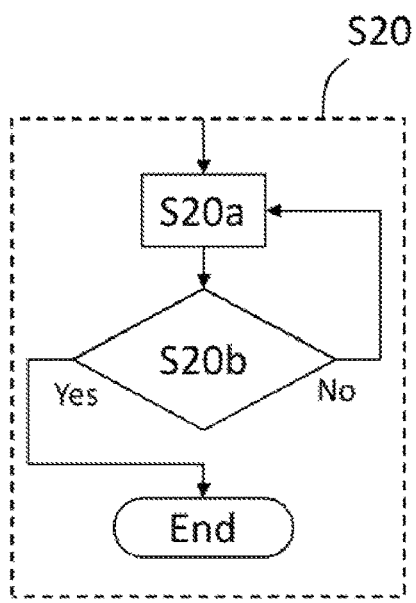

Alternatively, as schematically illustrated in FIG. 17, the second step S20 may comprise a first substep S20a of continuously or periodically monitoring body posture of the occupant during motion of at least a portion of the backrest and/or headrest backwards, a second substep S20b of comparing the detected body posture with an acceptable body posture in view of open airway of the occupant. When the detected body posture is sufficiently close to the acceptable body posture (Yes), the method includes the step of stopping the rearwards motion of the backrest and/or headrest, and when the detected body posture is insufficiently close to the acceptable body posture (No), the method continues the rearwards motion of the backrest and/or headrest.

Figure 18:
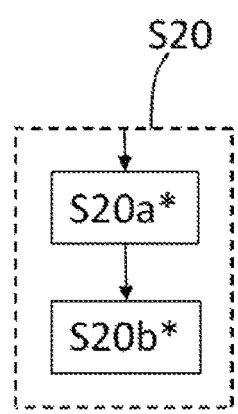

In addition, with reference to FIG. 18, the second step S20 may alternatively, or in combination with the method steps of FIG. 17, comprise a first substep S20a* of detecting an occupancy status of a vehicle seat 15 located behind the seat 14 of the occupant 18 and determining a reclined seat position taking into account the detected occupancy status of the vehicle seat 15 located behind the seat 14 of the occupant 18. The second step S20 may then involve second sub step S20b* of moving at least a portion of the backrest and/or headrest backwards until arriving at the reclined seat position determined taking into account the detected occupancy status of the vehicle seat 15 located behind the seat 14 of the occupant 18. Thereby, the risk that the legs of a further occupant 19 sitting behind the occupant 18 are wedged by the backrest 14b is reduced, while still being able to exploit the space behind the seat 14 in those cases when no further occupant 19 is available. The occupancy status of a vehicle seat 15 located behind the seat 14 may for example be detected by means of an image detector 17, ultrasonic transducer, laser scanner, etc., or be means of a seat occupancy sensors, such as a weight or deflection sensor arranged within the seat 15, or the like.

The present disclosure has been presented above with reference to specific embodiments. However, other embodiments than the above described are possible and within the scope of the disclosure. Different method steps than those described above, performing the method by hardware or software, may be provided within the scope of the disclosure.

The processor(s) associated with the control system 42 may be or include any number of hardware components for conducting data or signal processing or for executing computer code stored in memory. The system may have an associated memory, and the memory may be one or more devices for storing data and/or computer code for completing or facilitating the various methods described in the present description. The memory may include volatile memory or non-volatile memory. The memory may include database components, object code components, script components, or any other type of information structure for supporting the various activities of the present description. According to an exemplary embodiment, any distributed or local memory device may be utilized with the systems and methods of this description. According to an exemplary embodiment the memory is communicably connected to the processor (e.g., via a circuit or any other wired, wireless, or network connection) and includes computer code for executing one or more processes described herein.

The control system 42 may thus comprise a processor configured to perform the steps of the method described with reference to any of FIGS. 14-18. Similarly, a computer program may be provided that comprises instructions which, when the program is executed by a computer, cause the computer to carry out the steps of the method described with reference to any of FIGS. 14-18.

It will be appreciated that the above description is merely exemplary in nature and is not intended to limit the present disclosure, its application or uses. While specific examples have been described in the specification and illustrated in the drawings, it will be understood by those of ordinary skill in the art that various changes may be made and equivalents may be substituted for elements thereof without departing from the scope of the present disclosure as defined in the claims. Reference signs mentioned in the claims should not be seen as limiting the extent of the matter protected by the claims, and their sole function is to make claims easier to understand.

What is claimed is:

1. A computer-implemented method for moving an occupant of a vehicle seat to open airway position after a vehicle crash event, the vehicle seat having a seat cushion, a backrest and a headrest, the method comprising:
   detecting occurrence of a vehicle crash event, and
   moving at least a portion of the backrest and/or headrest backwards and pulling an occupant of the vehicle seat backwards towards the backrest by powered retraction of a seat belt of the occupant by means of a seat belt retractor.

2. The computer-implemented method according to claim 1, wherein the method comprises an intermediate step of waiting a certain time period after the step of detecting occurrence of a vehicle crash event, and before the step of moving at least a portion of the backrest and/or headrest backwards and pulling an occupant of the vehicle seat backwards towards the backrest.

3. The computer-implemented method according to claim 1,
   wherein the method comprises an intermediate step of obtaining information about airway status of the occupant, and wherein the method progresses to said step of moving at least a portion of the backrest and/or headrest backwards and pulling an occupant of the vehicle seat backwards towards the backrest when the detected airway status indicates blocked or hindered airway, and/or
   wherein the method comprises an intermediate step of obtaining information about level of consciousness of the occupant, and wherein the method progresses to said step of moving at least a portion of the backrest and/or headrest backwards and pulling an occupant of the vehicle seat backwards towards the backrest when the detected level of consciousness of the occupant is low or non-existing, and/or
   wherein the method comprises an intermediate step of obtaining information about values of one or more health parameters associated with the respiratory and/or cardiovascular systems of the occupant, and wherein the method progresses to said step of moving at least a portion of the backrest and/or headrest backwards and pulling an occupant of the vehicle seat backwards towards the backrest when the detected values of the one or more health parameters is outside of a predetermined range, and/or
   wherein the method comprises an intermediate step of obtaining information about body posture of the occupant, and wherein the method progresses to said step of moving at least a portion of the backrest and/or headrest backwards and pulling an occupant of the vehicle seat backwards towards the backrest when the detected body posture indicates blocked airway.

4. The computer-implemented method according to claim 1,
   wherein the moving of at least a portion of the backrest and/or headrest backwards is continued until arriving at a predetermined reclined seat position, or
   wherein the method comprises monitoring body posture of the occupant during moving of at least a portion of the backrest and/or headrest backwards and pulling the occupant of the vehicle seat backwards towards the backrest, and stopping the moving and pulling operation when the monitored body posture corresponds to an acceptable body posture in view of open airway of the occupant.

5. The computer-implemented method according to claim 4, wherein the method comprises detecting an occupancy status of a vehicle seat located behind the seat of the occupant, and determining the reclined seat position taking into account the detected occupancy status of the vehicle seat located behind the seat of the occupant.

6. The computer-implemented method according to claim 1, wherein the step of moving at least a portion of the backrest and/or headrest backwards involves performing one, two, three, or all of the following activities:
   folding the backrest backwards around a first pivot shaft located in an intersection region of the seat cushion and backrest,
   moving the headrest backwards,
   tilting the seat cushion backwards,
   adjusting a lumbar support arrangement or multi-contour arrangement of the vehicle seat for protruding more towards a lumbar region and/or back region of the occupant of the vehicle seat.

7. The computer-implemented method according to claim 6, wherein the backrest includes a second pivot shaft arranged in a region between the first pivot shaft and the headrest, and wherein the step of moving at least a portion of the backrest and/or headrest backwards additionally involves folding the backrest backwards around the second pivot shaft.

8. The computer-implemented method according to claim 1, wherein the vehicle seat includes one or more power actuators configured for adjusting the position of the backrest and/or headrest, and wherein the step of moving at least a portion of the backrest and/or headrest backwards involves controlling operation of said one or more power actuators for moving at least a portion of the backrest and/or headrest backwards.

9. The computer-implemented method according to claim 1, wherein a seat belt associated with the vehicle seat has a first attachment point for fastening a waist portion of the seat belt to the seat or vehicle chassis, and a second attachment point for fastening a chest portion of the seat belt to the seat or vehicle chassis, wherein the seat belt retractor is located at the second attachment point and configured for powered retraction or tensioning of the chest portion of the seat belt, and wherein the second attachment point is arranged:
   at the B-pillar of the vehicle chassis, or
   at the floor of the vehicle chassis, or
   at an interior side of the roof of the vehicle chassis, or
   integrated in the vehicle seat, in particular in the backrest or headrest of the vehicle seat.

10. The computer-implemented method according to claim 9, wherein the backrest or headrest comprises a seat belt guide configured for guiding or deflecting the chest portion of the seat belt along its path towards the seat belt retractor.

11. The computer-implemented method according to claim 1, wherein the step of moving at least a portion of the backrest and/or headrest backwards and pulling an occupant of the vehicle seat backwards towards the backrest by powered retraction of the seat belt is performed by, during a first half of the motion sequence, primarily pulling the occupant of the vehicle seat backwards towards the backrest by powered retraction of the seat belt while keeping the backrest and/or headrest relatively stationary, and subsequently during a second half of the motion sequence, primarily moving at least a portion of the backrest and/or headrest backwards while ensuring that the occupant remains in close contact with, or adjacent to, the backrest and/or headrest.

12. A vehicle seat system for moving an occupant of a vehicle seat to an open airway position after a vehicle crash event, the vehicle seat system comprising:
   a seat having a seat cushion, a backrest and a headrest, wherein the seat further has one or more power actuators configured for adjusting a motion position of the backrest and/or headrest,
   a seat belt arrangement having a seat belt and a seat belt retractor, wherein the seat belt arrangement further has power source drivingly connected to the seat belt retractor for enabling powered retraction, and
   an electronic control system operatively connected to the one or more power actuators of the seat and power source of the seat belt arrangement,
   wherein the control system is configured for:
   determining occurrence of a vehicle crash event, and
   controlling operation of the one or more power actuators of the seat for moving at least a portion of the backrest and/or headrest backwards, and controlling operation of the power source of the seat belt retractor for pulling the occupant of the vehicle seat backwards towards the backrest.

13. The vehicle seat system according to claim 12, wherein the vehicle seat has:
   a first pivot shaft located in an intersection region of the seat cushion and backrest and configured for enabling folding of the backrest backwards, and
   a second pivot shaft arranged in a region of the backrest located between the first pivot shaft and the headrest and configured for enabling folding of an upper portion of the backrest located between the second pivot shaft and headrest backwards.

14. The vehicle seat system according to claim 12, wherein the seat belt has a first attachment point for fastening a waist portion of the seat belt to the seat or vehicle chassis, and a second attachment point for fastening a chest portion of the seat belt to the seat or vehicle chassis, wherein the seat belt retractor is located at the second attachment point and configured for powered winding or tensioning of the chest portion of the seat belt, and wherein the second attachment point is arranged:
   at the B-pillar of the vehicle chassis, or
   at the floor of the vehicle chassis, or
   at an interior side of the roof of the vehicle chassis, or
   integrated in the vehicle seat, in particular in the backrest or headrest of the vehicle seat.

15. The vehicle seat system according to claim 12,
   wherein the control system is configured for obtaining information about airway status of the occupant, and for controlling motion of at least a portion of the backrest and/or headrest backwards and controlling pulling an occupant of the vehicle seat backwards towards the backrest when the detected airway status indicates blocked or hindered airway, and/or
   wherein the control system is configured for obtaining information about level of consciousness of the occupant, and controlling motion of at least a portion of the backrest and/or headrest backwards and controlling pulling an occupant of the vehicle seat backwards towards the backrest when the detected level of consciousness of the occupant is low or non-existing, and/or
   wherein the control system is configured for obtaining information about values of one or more health parameters associated with the respiratory and/or cardiovascular systems of the occupant, and controlling motion of at least a portion of the backrest and/or headrest backwards and controlling pulling an occupant of the vehicle seat backwards towards the backrest when the detected values of the one or more health parameters is outside of a predetermined range, and/or
   wherein the control system is configured for obtaining information about body posture of the occupant, and controlling motion of at least a portion of the backrest and/or headrest backwards and controlling pulling an occupant of the vehicle seat backwards towards the backrest when the detected body posture indicates blocked airway.

16. A vehicle seat system for moving an occupant of a vehicle seat to an open airway position after a vehicle crash event, the vehicle seat system comprising:
   a seat having a seat cushion, a backrest and a headrest, wherein the seat further has one or more power actuators configured for adjusting a motion position of the backrest and/or headrest,
   a seat belt arrangement having a seat belt and a seat belt retractor, wherein the seat belt arrangement further has power source drivingly connected to the seat belt retractor for enabling powered retraction, and
   an electronic control system operatively connected to the one or more power actuators of the seat and power source of the seat belt arrangement,
   wherein the control system is configured for performing the method steps of claim 1.

* * * * *